(12) United States Patent
Toumpoulis et al.

(10) Patent No.: US 12,123,057 B2
(45) Date of Patent: Oct. 22, 2024

(54) METHODS FOR DETECTING AN ANEURYSM

(71) Applicant: TWOBULL MEDITHERAPY P.C., Patra (GR)

(72) Inventors: Ioannis Toumpoulis, Kato Achaia (GR); Stavros Toumpoulis, Kato Achaia (GR)

(73) Assignee: TWOBULL MEDITHERAPY P.C., Patra (GR)

( * ) Notice: Subject to any disclaimer, the term of this patent is extended or adjusted under 35 U.S.C. 154(b) by 688 days.

(21) Appl. No.: 16/950,825

(22) Filed: Nov. 17, 2020

(65) Prior Publication Data

US 2021/0102258 A1 Apr. 8, 2021

Related U.S. Application Data

(63) Continuation of application No. PCT/EP2018/062897, filed on May 17, 2018.

(51) Int. Cl.
*C12Q 1/6883* (2018.01)
*C12Q 1/6886* (2018.01)

(52) U.S. Cl.
CPC ......... *C12Q 1/6883* (2013.01); *C12Q 1/6886* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 2009/0226905 A1* | 9/2009 | Joubert | ............ | G01N 33/57419 435/7.1 |
| 2015/0203916 A1* | 7/2015 | Ikonomidis | ............... | C12Q 1/66 506/9 |

FOREIGN PATENT DOCUMENTS

| | | |
|---|---|---|
| EP | 1947194 A1 | 7/2008 |
| EP | 2599860 A1 | 6/2013 |
| JP | 2007-020586 A | 2/2007 |
| WO | WO 2017/158358 | 9/2017 |

OTHER PUBLICATIONS

Liu et al Clinical Immunology. 2004. 112: 225-230 (Year: 2004).*
Coleman, R. Drug Discovery Today. 2003. 8: 233-235 (Year: 2003).*
Min et al BMC Genomics. 2010. 11:96 (Year: 2010).*
Palmer (BMC Genomics. 2006. 7:115 (Year: 2006).*
Hanke et al. Clinical Chemistry. 2007. 53: 2070-2077 (Year: 2007).*
Chen et al Molecular & Cellular Proteomics. 2002. 1: 304-313 (Year: 2002).*
Zhang et al Nature. Sep. 18, 2014. 513(7518): 382-387 (Year: 2014).*
Vogel et al Nature Review Genet. Mar. 2012. 13(4): 227-232 (Year: 2012).*
Toumpoulis et al Ann Thorac Surg. Aug. 2009. 88(2): 506-513 (Year: 2009).*
Sabatino et al. J Biol Regulators & Homeostatic Agents. 2013. 27(3): 729-738 (Year: 2013).*
Notice of Reasons for Refusal dated Jan. 5, 2023 issued for Japanese Patent Application No. 2020-564408; with English translation, 11 pages.
Agata, et al., "Matrix metalloproteinases (MMPs), the main extracellular matrix (ECM) enzymes in collagen degradation, as a target for anticancer drugs," Journal of Enzyme Inhibition and Medicinal Chemistry, vol. 31 (S1), pp. 177-183, XP055487499 (2016).
Angulo, et al., "Detection and molecular staging of bladder cancer using real-time RT-PCR for gelatinases (MMP-2, MMP-9) and TIMP-2 in peripheral blood," Actas Urologicas Espanolas, vol. 35, pp. 127-136, XP055487492 (2011).
Cheon, et al., "A Collagen-Remodeling Gene Signature Regulated by TGF-ß Signaling is Associated with Metastasis and Poor Survival in Serous Ovarian Cancer," Clinical Cancer Research, vol. 20, No. 3, pp. 711-723, XP055168020 (2013). Huusko, et al., "Elevated messenger RNA expression and plasma protein levels of osteopontin and matrix metalloproteinase types 2 and 9 in patients with ascending aortic aneurysms", The Journal of Thoracic and Cardiovascular Surgery, vol. 145, No. 4, pp. 1117-1123, XP029002510 (published online 2012).
International Search Report, mailed Aug. 29, 2018, for International Application No. PCT/EP2018/062897.
Kossenkov, et al., "Peripheral Immune Cell Gene Expression Predicts Survival of Patients with Non-Small Cell Lung Cancer," PLOS ONE, vol. 7, No. 3, p. e34392, XP055487496 (2012).
Kroupis, et al, "Development and applications of a real-time quantitative RT-PCR method (QRT-PCR) for BRCA1 mRNA," Clinical Biochemistry, vol. 38, Issue 1, pp. 50-57 (2005).

(Continued)

*Primary Examiner* — Carla J Myers
(74) *Attorney, Agent, or Firm* — Squire Patton Boggs (US)LLP

(57) ABSTRACT

The present application provides an in vitro method for determining the degradation of the extracellular matrix (ECM) in a subject, the method comprising determining in an isolated sample from the subject the level of an expression product of at least one gene selected from the group consisting of collagen type V alpha 1 chain (COL5A1), transforming growth factor beta-1 (TGFB1), integrin subunit alpha 4 (ITGA4), integrin subunit beta 1 (ITGB1), matrix metallopeptidase 2 (MMP2), matrix metallopeptidase 9 (MMP9) and bone morphogenetic protein 1 (BMP1), the at least one gene being determined optionally in combination with one or both of collagen type XI alpha 1 chain (COL11A1) and collagen type V alpha 2 chain (COL5A2), wherein when the level of the expression product(s) is(are) higher than a reference value this is indicative of a degraded ECM. Methods for the diagnosis and prognosis of cancer and aneurysms are also provided. Furthermore, means for determining the level of expression product of the genes in the above diagnosis or prognosis methods are also provided, as well as kits containing said means.

3 Claims, 12 Drawing Sheets
Specification includes a Sequence Listing.

(56) References Cited

OTHER PUBLICATIONS

Livak and Schmittgen, "Analysis of Relative Gene Expression Data Using Real-Time Quantitative PCR and the $2^{-\Delta\Delta C_T}$ Method," Methods, vol. 25, Issue 4, pp. 402-408 (2001).

Pérez-Callejo, et al., "Liquid biopsy based biomarkers in non-small cell lung cancer for diagnosis and treatment monitoring," Translational Lung Cancer Research, vol. 5, No. 5, pp. 455-465, XP055474064 (2016).

Qiu, et al., "RNA sequencing identifies crucial genes in papillary thyroid carcinoma (PTC) progression," Experimental and Molecular Pathology, vol. 100, No. 1, pp. 151-159, XP029398929 (published online 2015).

Sabatino, et al., "Transcriptional Profile Characterization for the Identification of Peripheral Blood Biomarkers in Patients with Cerebral Aneurysms," Journal of Biological Regulators and Homeostatic Agents, vol. 27, No. 3, pp. 729-738, XP009506340 (2013).

Sheu, et al., "Development of a membrane array-based multimarker assay for detection of circulating cancer cells in patients with non-small cell lung cancer," International Journal of Cancer, vol. 119, No. 6, pp. 1419-1426, XP055487673 (2006).

Black, et al: "Preliminary biomarkers for identification of human ascending thoracic aortic aneurysm", Journal of the American Heart Association 2013; vol. 2, e000138, pp. 1-12.

Ian D. Danford, "Characterizing the "POAGome": a bioinformatics-driven approach to primary open-angle glaucoma", Prog Retin Eye Res; May 2017; vol. 58, pp. 89-114.

\* cited by examiner

METHODS FOR DETECTING AN ANEURYSM

CROSS REFERENCE TO RELATED APPLICATIONS

This application is a continuation of International Patent Application No. PCT/EP2018/062897, filed May 17, 2018, the disclosure of which is incorporated herein by reference in its entirety.

SEQUENCE LISTING

The present application contains a Sequence Listing which has been submitted in ASCII format via EFS-Web and is hereby incorporated by reference in its entirety. Said ASCII copy, created on Nov. 17, 2020, is named 088927_0102_SL.txt and is 6,394 bytes in size.

TECHNICAL FIELD

The present invention pertains to the field of diagnosis, in particular diagnosis in blood samples, and more particularly for the diagnosis and prognosis of cancer and aneurysms by detecting the degradation of the extracellular matrix.

BACKGROUND ART

Cancer is representing a common and increasing cause of death. It is estimated by the World Health Organization that during the next 2-3 decades cancer will be the leading cause of death worldwide. The most effective weapon to fight the increased mortality from cancer is early diagnosis. Many types of cancer could be treated effectively if detected in their early stages. This reality underlines the need to develop a simple, reliable and cost-effective set of molecular markers for the detection of cancer in the initial stages of carcinogenesis. Another important strategy in fighting cancer effectively is to identify early the patients at risk for developing metastasis in order to follow-up them more frequently as well as to apply more aggressive therapeutic interventions in this subgroup of patients.

Recent progress has also highlighted the importance of non-cellular components of the local microenvironments, or niches, especially the extracellular matrix (ECM), during cancer progression. The ECM is an amalgam of extracellular molecules secreted by support cells that provides structural and biochemical support to the surrounding cells. The mammalian ECM includes the interstitial matrix and the basement membrane. Interstitial matrix is present between various mammalian cells (i.e., in the intercellular spaces). Gels of polysaccharides and fibrous proteins fill the interstitial space and act as a compression buffer against the tensile stress applied on the ECM. Basement membranes are sheet-like depositions of ECM on which various epithelial cells rest. Each type of connective tissue in mammals has a type of ECM: collagen fibers and bone mineral comprise the ECM of bone tissue; reticular fibers and ground substance comprise the ECM of loose connective tissue; and blood plasma is the ECM of blood.

Although long viewed as a stable structure that plays a mainly supportive role in maintaining tissue morphology, the ECM is an essential part of the milieu of the resident cells that is surprisingly dynamic and versatile and influences fundamental aspects of cell biology. Cell adhesion, cell-to-cell communication and differentiation are common functions of the ECM. This pleiotropic aspect of ECM function depends on the highly dynamic structure of ECM and its remodeling as an effective mechanism whereby diverse cellular behaviors can be regulated. A major challenge in ECM biology is to understand the roles of the ECM in normal development and how disruption of ECM dynamics may contribute to diseases such as cancer.

Another example of disease that may be highly influenced by the alterations of the ECM is aortic aneurysm. In aortic aneurysms, there is a degradation of the ECM of the aortic wall leading initially to aortic dilatation and then to aneurysmal formation.

Aortic aneurysms are representing a significant clinical entity, which progresses asymptomatically until rupture or dissection occurs. It is a considerable leading cause of death in developed countries. The rupture of an aortic aneurysm, which is usually the first and simultaneously the last symptom, carries a mortality rate of 75%. It is estimated that the incidence of aortic aneurysms will continue to increase worldwide in the next years because of the aging of the general population. The pathogenesis and the molecular mechanisms leading to aneurysm formation are under investigation and, at present, there is no simple laboratory test that has the ability to reliably detect aortic aneurysms.

In view of the above epidemiologic data there is an urgent need to provide simple and reliable tests for the early diagnosis of cancer and aortic aneurysm, as well as methods for efficient follow-up of the patients in order to identify early the patients at risk for developing metastasis or relapsing patients. Furthermore, better strategies are generally needed to optimize treatment regimes for cancer and aneurysm patients.

DETAILED DESCRIPTION OF THE INVENTION

The inventors have surprisingly found that abnormal function or degradation of the ECM can be accurately detected by determining the level of expression of certain genes in peripheral blood. Overexpression of these particular set of genes in peripheral blood reveals the level of activation of the molecular mechanism which promotes the remodeling of the ECM with implications in cancer and aneurysm progression.

The fingerprint for detecting degradation or abnormal function of the ECM comprises the genes which are shown in table 1.

TABLE 1

Genetic fingerprint for determining degradation of the ECM.

| name | symbol | NCBI Reference Sequence |
|---|---|---|
| collagen type XI alpha 1 chain | COL11A1 | NG_008033.1 |
| collagen type V alpha 2 chain | COL5A2 | NG_011799.2 |
| collagen type V alpha 1 chain | COL5A1 | NG_008030.1 |
| transforming growth factor beta-1 | TGFB1 | NG_013364.1 |
| integrin subunit alpha 4 | ITGA4 | NG_050623.1 |
| integrin subunit beta 1 | ITGB1 | NG_029012.1 |
| matrix metallopeptidase 2 | MMP2 | NG_008989.1 |
| matrix metallopeptidase 9 | MMP9 | NG_011468.1 |
| bone morphogenetic protein 1 | BMP1 | NG_029659.1 |

Thus, a first aspect of the invention provides an in vitro method for determining the degradation of the extra cellular matrix (ECM) in a subject, the method comprising determining in an isolated sample from the subject the level of an expression product of at least one gene selected from the group consisting of the genes listed in table 1, wherein when the level of the expression product is higher than a reference value this is indicative of a disorganized/degraded ECM.

In the sense of the present invention the expression "degradation of the ECM" is also understood as remodeling resulting in disorganized ECM or abnormal ECM mechanical and dynamic properties.

The term "diagnosis" is known to the person skilled in the art. As used herein "diagnosis" is understood as becoming aware of a particular medical condition, complication; the determination of the nature of the condition; or the distinguishing of the condition from another. It refers both to the process of attempting to determine or identify the possible condition, and to the opinion reached by this process. A diagnosis, in the sense of diagnostic procedure, can be regarded as an attempt at classification of an individual's condition into separate and distinct categories that allow medical decisions about treatment and prognosis to be made. Subsequently, a diagnostic opinion is often described in terms of a condition.

"Prognosis" as used herein refers to the prediction of the probable progression and outcome of the disease as well as the monitoring of the disease progression.

In the present invention, the term "expression product" of a gene is to be understood as encompassing the mRNA product, full-length protein product or a proteolytic fragment thereof, depending on the detection technique to be used. Thus, when it is determined the "level of the expression product", it can refer to the level of mRNA, or to the level of the encoded full-length protein or to the level of a proteolytic fragment thereof.

The term "reference value" in the context of the present invention is to be understood as a predefined level of expression product of the genes in a sample or group of samples. This value is used as a threshold to discriminate subjects wherein the condition to be analysed is present from those wherein such condition is absent. The samples are taken from a well-defined control subject or group of control subjects having no degraded ECM and normal function thereof, that also means that the control subjects do not suffer from any condition that is related with abnormal function and/or degradation of the ECM. The skilled person in the art, making use of the general knowledge, is able to choose the subject or group of subjects more adequate for obtaining the reference value. Methods for obtaining the reference value from the group of subjects selected are well known in the state of the art. In one embodiment of the present invention, the reference value is determined from a subject or group of subjects that do not suffer from cancer or aneurysm. In a particular embodiment the reference value is determined from a healthy subject or group of healthy subjects.

In the sense of the present invention, the expression "higher than a reference value" is understood as any increase in the level of expression product, for example at least 1.2-fold, or 1.5-fold increase of expression product with respect to the reference value. In particular embodiments, "higher than a reference value" is understood as at least 2-fold increase of expression product with respect to the reference value.

In particular embodiments of the method of the invention, the level of expression product of at least COL11A1 and/or COL5A2 is determined. In another particular embodiment, the method comprises determining the level of an expression product of at least one gene selected from the group consisting of COL5A1, TGFB1, ITGA4, ITGB1, MMP2, MMP9 and BMP1, the at least one gene being determined optionally in combination with one or both of COL11A1 and COL5A2, wherein when the level of the expression product(s) is(are) higher than a reference value this is indicative of a degraded ECM. In one embodiment the expression products of both COL11A1 and COL5A2 are determined.

In one embodiment detecting the degradation of the ECM is performed by determining the level of expression product of at least three, at least four, at least five, at least six, at least seven, at least eight or at least nine of the genes disclosed in table 1. In a particular embodiment, the expression product of at least COL11A1, COL5A2, and MMP2 is determined.

In other particular embodiments the expression product of at least the following genes is determined: COL11A1, COL5A2, MMP2 and MMP9, or at least COL11A1, COL5A2, MMP2, MMP9 and BMP1, or at least COL11A1, COL5A2, MMP2, MMP9, BMP1 and ITGA4, or at least COL11A1, COL5A2, MMP2, MMP9, BMP1, ITGA4 and ITGB1, or at least COL11A1, COL5A2, MMP2, MMP9, BMP1, ITGA4, ITGB1 and COL5A1, or at least COL11A1, COL5A2, MMP2, MMP9, BMP1, ITGA4, ITGB1, COL5A1 and TGFB1. In another particular embodiment, expression product of the nine genes is determined.

The inventors have thus found that the above set of genes can adequately analyze the molecular mechanism which controls the remodeling of the ECM. Without wanting to be bound by theory, the inventors hypothesize that the increased expression and synthesis of minor fibril-forming collagens (collagen V alpha-2, collagen V alpha-1 and collagen XI alpha-1) contributes to the formation of smaller size and diameter heterotypic fibrils of major fibril-forming collagens (Collagen I and Collagen III). The minor fibril-forming collagens have the ability to inhibit the assembly of major fibril-forming collagens through steric hindrance with their large globular amino-terminal domain, which retains in part in the final protein complex. In addition, the released large globular amino-terminal domains contain a well-characterized heparin binding domain, which can interact with specific integrin receptors, which in turn control the expression and activity of matrix metalloproteinases, which are responsible for the degradation of the components of the ECM. This molecular mechanism results in thinner, disorganized and degraded ECM, and thus, more susceptible to dilatation and aortic aneurysm formation, as well as to cancer growth and metastasis.

The extensive research performed by the inventors has also resulted in identifying further genetic markers that may provide additional diagnosis information on the degradation of the ECM. These genes are listed in table 1bis. Thus, in a particular embodiment of the invention detecting the degradation of the ECM is performed by additionally determining the level of expression product of at least one gene selected from the genes in table ibis. In some embodiment detecting the degradation of the ECM is performed by determining the level of expression product of at least one gene selected from the genes in table 1bis in addition to at least one gene disclosed in table 1 or any of their combinations as defined above.

TABLE 1bis

Genetic fingerprint for determining degradation of the ECM.

| name | symbol | NCBI Reference Sequence |
| --- | --- | --- |
| Integrin subunit alpha 3 | ITGA3 | NG_029107.2 |
| integrin subunit alpha 6 | ITGA6 | NG_008853.1 |
| Tissue inhibitor of matrix metallopeptidase 1 | TIMP1 | NG_012533.1 |
| collagen type I alpha 1 chain | COL1A1 | NG_007400.1 |
| collagen type III alpha 1 chain | COL3A1 | NG_007404.1 |
| collagen type I alpha 2 chain | COL1A2 | NG_007405.1 |

The biological sample isolated from the subject may be any tissue, or a bodily fluid such as blood, plasma, saliva, urine, cerebrospinal fluid, or semen. However, in one preferred embodiment of the invention the biological sample is peripheral blood. This is important because it greatly speeds up and simplifies the detection method, plus it is non-invasive. It is indeed surprising that differential expression of the set of genes disclosed in table 1 may be found in peripheral blood of subjects having a degraded ECM.

In one embodiment the expression product of the genes which is determined in the context of the present invention is mRNA. In preferred embodiments, the amount of mRNA of the tested subject is quantified and compared to the reference value, which is the amount of the same mRNA of the control subject or the average amount of mRNA of the group of control subjects. The known mRNA sequences for the genes comprising the fingerprint of the invention are disclosed in table 2 and the known protein sequences of the same genes are disclosed in table 2p. It is noted that several transcripts are possible for some of the genes, for example for COL11A1. However, the method of the invention preferably determines all possible transcripts of the genes, so that all transcribed mRNA from a particular gene is determined.

TABLE 2 mRNA sequences for the genes of tables 1 and 1bis

| mRNA transcript | NCBI Reference Sequence |
| --- | --- |
| COL11A1 variant A | NM_001854.3 |
| COL11A1 variant B | NM_080629.2 |
| COL11A1 variant C | NM_080630.3 |
| COL11A1 variant E | NM_001190709.1 |
| COL11A1 variant F | NR_134980.1 |
| COL5A2 | NM_000393.4 |
| COL5A1 variant 1 | NM_000093.4 |
| COL5A1 variant 2 | NM_001278074.1 |
| TGFB1 | NM_000660.6 |
| ITGA4 variant 1 | NM_000885.5 |
| ITGA4 variant 2 | NM_001316312.1 |
| ITGB1 variant 1A | NM_002211.3 |
| ITGB1 variant 1B | NM_033668.2 |
| ITGB1 variant 1E | NM_133376.2 |
| MMP2 variant 1 | NM_004530.5 |
| MMP2 variant 2 | NM_001127891.2 |
| MMP2 variant 3 | NM_001302508.1 |
| MMP2 variant 4 | NM_001302509.1 |
| MMP2 variant 5 | NM_001302510.1 |
| MMP9 | NM_004994.2 |
| BMP1 variant 1 | NM_001199.3 |
| BMP1 variant 3 | NM_006129.4 |
| BMP1 variant 4 | NR_033403.1 |
| BMP1 variant 5 | NR_033404.1 |
| ITGA3 | NM_002204.3 |
| ITGA6 variant 1 | NM_001079818.2 |
| ITGA6 variant 2 | NM_000210.3 |
| ITGA6 variant 3 | NM_001316306.1 |
| TIMP1 | NM_003254.2 |
| COL1A1 | NM_000088.3 |
| COL3A1 | NM_000090.3 |
| COL1A2 | NM_000089.3 |

TABLE 2p

Protein sequences for the genes of tables 1 and 1bis

| Protein | NCBI Reference Sequence |
| --- | --- |
| COL11A1 isoform A | NP_001845.3 |
| COL11A1 isoform B | NP_542196.2 |
| COL11A1 isoform C | NP_542197.3 |
| COL11A1 isoform E | NP_001177638.1 |
| COL5A2 | NP_000384.2 |

TABLE 2p-continued

Protein sequences for the genes of tables 1 and 1bis

| Protein | NCBI Reference Sequence |
| --- | --- |
| COL5A1 isoform 1 | NP_000084.3 |
| COL5A1 isoform 2 | NP_001265003.1 |
| TGFB1 | NP_000651.3 |
| ITGA4 isoform 1 | NP_000876.3 |
| ITGA4 isoform 2 | NP_001303241.1 |
| ITGB1 isoform 1A | NP_002202.2 |
| ITGB1 isoform 1D | NP_391988.1 |
| ITGB1 isoform 1E | NP_596867.1 |
| MMP2 isoform 1 | NP_004521.1 |
| MMP2 isoform 2 | NP_001121363.1 |
| MMP2 isoform 3 | NP_001289437.1 |
| MMP2 isoform 4 | NP_001289438.1 |
| MMP2 isoform 5 | NP_001289439.1 |
| MMP9 | NP_004985.2 |
| BMP1 isoform 1 | NP_001190.1 |
| BMP1 isoform 3 | NP_006120.1 |
| ITGA3 | NP_002195.1 |
| ITGA6 isoform a | NP_001073286.1 |
| ITGA6 isoform b | NP_000201.2 |
| ITGA6 isoform c | NP_001303235.1 |
| TIMP1 | NP_003245.1 |
| COL1A1 | NP_000079.2 |
| COL3A1 | NP_000081.1 |
| COL1A2 | NP_000080.2 |

Determining the amount of mRNA can be performed by any method known to the skilled person, provided that said method permits the detection and quantification of mRNA in a biological sample. Included among the examples of these procedures are PCR, quantitative real-time PCR (QPCR), multiplex PCR, NASBA, LCR, RT-PCR, RNA sequencing, array hybridization or "Northern" transfer, or combinations of these. In most methods of detection and quantification of RNA mentioned above, before performing this procedure it is necessary to convert the RNA to complementary DNA (cDNA). This conversion is accomplished by known techniques by skilled in the art, such as reverse transcription, among others.

In a particular embodiment of the invention the level of an expression product of the genes is determined by quantification of the mRNA by reverse transcription followed by real-time quantitative PCR. For this technique, as well as for many other techniques for detecting/quantifying gene expression, use of amplification primers is required. In a preferred embodiment of the present invention, the primer sequences are derived from the transcript sequences of the genes disclosed in table 2. In particular embodiments, the primers used for determining the level of an expression product of the genes, namely mRNA are selected from those shown in table 3. Determining the level of mRNA of the above genes by reverse transcription followed by real-time quantitative PCR is described in detail in the examples below.

TABLE 3

Primers used for determining the mRNA of the genes of tables 1 and 1bis

| mRNA target | Forward primer | Reverse primer |
| --- | --- | --- |
| COL1A1 | 5'-CTCTGACTGGAAGAGTGGAGAGTA-3' (SEQ ID NO: 1) | 5'-TTGGTGGTTTTGTATTCAATCACT-3' (SEQ ID NO: 2) |
| COL1A2 | 5'-CATCCCAGCCAAGAACTGGT-3' (SEQ ID NO: 3) | 5'-ACTGGGCCAATGTCCACAAA-3' (SEQ ID NO: 4) |
| COL3A1 | 5'-AGTGACCGACAAAATTCCAGTTAT-3' (SEQ ID NO: 5) | 5'-CTTTTACTGGTGAGCACAGTCATT-3' (SEQ ID NO: 6) |
| COL5A1 | 5'-TTCAAGCGTGGGAAACTGCT-3' (SEQ ID NO: 7) | 5'-GGGAGAAGCCTTCACTGTCC-3' (SEQ ID NO: 8) |
| COL5A2 | 5'-TGAGTTGTGGAGCTGACTCTAATC-3' (SEQ ID NO: 9) | 5'-TAACAGAAGCATAGCACCTTTCAG-3' (SEQ ID NO: 10) |
| COL11A1 | 5'-GAAATTGTACCTTGGTGCCACCAAC-3' (SEQ ID NO: 11) | 5'-GGATGGATGAGAATGAGCACCATAT-3' (SEQ ID NO: 12) |
| ITGA3 | 5'-ACAAGGATGACTGTGAGCGG-3' (SEQ ID NO: 13) | 5'-CTGCCTACCTGCATCGTGTA-3' (SEQ ID NO: 14) |
| ITGA4 | 5'-GTCTTTGTCACTAAAATGTTCCCCA-3' (SEQ ID NO: 15) | 5'-CAGCAAGAGCGGACCTGA-3' (SEQ ID NO: 16) |
| ITGA6 | 5'-GTTGGGAGGGTGGTTCAACA-3' (SEQ ID NO: 17) | 5'-CGAATCCCATTGCTTTGGCAC-3' (SEQ ID NO: 18) |
| ITGB1 | 5'-ATCAGACGCGCAGAGGAGG-3' (SEQ ID NO: 19) | 5'-TGCTGTTCCTTTGCTACGGT-3' (SEQ ID NO: 20) |
| MMP2 | 5'-CGCATCTGGGGCTTTAAACAT-3' (SEQ ID NO: 21) | 5'-CTGTCTGGGGCAGTCCAAAG-3' (SEQ ID NO: 22) |
| MMP9 | 5'-TTCAGGGAGACGCCCATTTC-3' (SEQ ID NO: 23) | 5'-TCGCTGGTACAGGTCGAGTA-3' (SEQ ID NO: 24) |
| TIMP1 | 5'-CTTCTGGCATCCTGTTGTTG-3' (SEQ ID NO: 25) | 5'-GGTATAAGGTGGTCTGGTTG-3' (SEQ ID NO: 26) |
| BMP1 | 5'-CCATGACAACAAGCACGACTG-3' (SEQ ID NO: 27) | 5'-GCCACAATGACCCACTCACA-3' (SEQ ID NO: 28) |
| TGFB1 | 5'-GAGCCTGAGGCCGACTACTA-3' (SEQ ID NO: 29) | 5'-GGGTTCAGGTACCGCTTCTC-3' (SEQ ID NO: 30) |
| ACTB (Beta-actin) | 5'-AGCATTGCTTTCGTGTAAATTATG-3' (SEQ ID NO: 31) | 5'-GTGTGCACTTTTATTCAACTGGTC-3' (SEQ ID NO: 32) |

The present invention requires comparing the level of expression of the expressed products of the genes with a reference value. The reference value, as mentioned above, is obtained from a control subject or group of control subjects. The skilled person may use any available method to establish the described comparison. For instance, as method of relative quantification, the $2^{-\Delta\Delta Ct}$ of Livak and Schmittgen may be employed (*Methods*, 2001 vol. 25, issue 4, p. 402-8).

In another embodiment, microarrays are used which include one or more probes corresponding to one or more of biomarkers identified in Table 2. This method results in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

In embodiments the expression product of the genes which is determined in the context of the present invention is the full-length protein encoded by the genes, or a fragment of said protein. In particular embodiment of the methods provided by the present invention, the level of the protein markers or fragments thereof is determined by a quantitative test selected from the group consisting of an immunological test, bioluminescence, fluorescence, chemiluminescence, electrochemistry and mass spectrometry. In some embodiments the proteins to be determined are those shown in table 2p.

In one embodiment the level of encoded protein or fragment thereof is detected by mass spectrometry, for example, by Shotgun Liquid Chromatography Mass Spectrometry (LC-MS/MS) or Multiple reaction monitoring (MRM) mass spectrometry.

In an alternative embodiment, the level of expression is determined by immunochemistry.

The term "immunochemistry" as used herein refers to a variety of techniques for detecting antigens (in the present case any of the proteins encoded by the above genes or antigenic fragments thereof) in a sample by exploiting the principle of antibodies binding specifically to the target protein(s). Visualizing an antibody-antigen interaction can be then accomplished in a number of ways, usually by conjugating the antibody to an enzyme, such as peroxidase, that can catalyse a colour-producing reaction, or to a fluorophore, such as fluorescein or rhodamine. The immunochemistry technique can be direct or indirect.

Suitable immunoassay procedures include enzyme-linked immunosorbent assays (ELISA, such as multiplex ELISA), enzyme immunodot assay, agglutination assay, antibody-antigen-antibody sandwich assay, antigen-antibody-antigen sandwich assay, immunocromatography, or other immunoassay formats well-known to the ordinarily skilled artisan, such as radioimmunoassay, as well as protein microarray formats. In one embodiment, the level of the protein is determined by an immunoassay. In another embodiment, the level of expression of protein is determined by ELISA.

The term "antibody or a fragment thereof able to bind to the target protein(s)" is to be understood as any immunoglobulin or fragment thereof able to selectively bind the target protein(s) referred in the aspects and embodiments of the present invention. It includes monoclonal and polyclonal antibodies. The term "fragment thereof" encompasses any part of an antibody having the size and conformation suitable to bind an epitope of the target protein. Suitable fragments include F(ab), F(ab') and Fv. An "epitope" is the part of the antigen being recognized by the immune system (B-cells, T-cells or antibodies).

Another aspect of the invention refers to use of means for determining the level of expression product of at least one gene selected from the group consisting of the genes of table 1 in the method for detecting degradation of the ECM as defined above. In a particular embodiment, the means are at least for determining the level of expression product of COL11A1 and/or COL5A2. In another particular embodiment, the means are for determining the level of expression product of at least one gene selected from the group consisting of COL5A1, TGFB1, ITGA4, ITGB1, MMP2, MMP9 and BMP1, optionally in combination with one or both of COL11A1 and COL5A2. Preferably means are for both COL11A1 and COL5A2. In particular embodiments the means are for determining the level of an expression product of at least three genes, at least four genes, at least five genes, at least six genes, at least seven genes, at least eight or at least nine genes selected from the group of genes disclosed in table 1. In other particular embodiments, the means include means for determining the level of an expression product of at least the following genes: COL11A1, COL5A2, and MMP2, or for at least COL11A1, COL5A2, MMP2 and MMP9, or for at least COL11A1, COL5A2, MMP2, MMP9 and BMP1, or for at least COL11A1, COL5A2, MMP2, MMP9, BMP1 and ITGA4, or for at least COL11A1, COL5A2, MMP2, MMP9, BMP1, ITGA4 and ITGB1, or for at least COL11A1, COL5A2, MMP2, MMP9, BMP1, ITGA4, ITGB1 and COL5A1, or for at least COL11A1, COL5A2, MMP2, MMP9, BMP1, ITGA4, ITGB1, COL5A1 and TGFB1. In another embodiment the means are for determining the level of an expression product of all the genes disclosed in table 1. In another embodiment the means are for determining the level of an expression product of at least one gene disclosed in table ibis in addition to at least one gene disclosed in table 1 or any of their combinations as defined above.

In particular embodiments the means are for determining mRNA. In one embodiment the means comprise amplification primers. In particular embodiments the primers are in each case those shown in table 3.

In other embodiments the means are for the means are for determining proteins or fragments thereof. On particular embodiments the means are antibodies or fragments thereof that specifically bind to the target protein(s).

In another embodiment the means form part of a kit. Furthermore, the present invention also provides the use of kits comprising means for determining the level of expression product as defined above for performing any of the methods provided herein. The kits may comprise said means and instructions for their use in detecting the degradation of the ECM in a subject. The instruction may include information regarding thresholds for determining the degradation of the ECM, the extent of such degradation and/or reference values.

In another aspect of the invention provides for use of an expression product of at least one gene selected from the group consisting of the genes of table 1 for detecting degradation of the ECM in a subject. In some embodiments at least COL11A1 and/or COL5A2 are the selected biomarkers. In another embodiment the use of an expression product of at least one gene selected from the group consisting of COL5A1, TGFB1, ITGA4, ITGB1, MMP2, MMP9 and BMP1, optionally in combination with one or both of COL11A1 and COL5A2, as in vitro biomarkers for detecting degradation of the ECM in a subject. Preferably, both COL11A1 and COL5A2 are among the selected biomarkers.

In one embodiment the biomarkers for detecting the degradation of the ECM in a subject are the expression products of at least three, at least four, at least five, at least six, at least seven, at least eight or at least nine of the genes disclosed in table 1. In a particular embodiment, at least COL11A1, COL5A2, and MMP2 are selected. In other particular embodiments the following genes are selected: COL11A1, COL5A2, MMP2 and MMP9, or at least COL11A1, COL5A2, MMP2, MMP9 and BMP1, or at least COL11A1, COL5A2, MMP2, MMP9, BMP1 and ITGA4, or at least COL11A1, COL5A2, MMP2, MMP9, BMP1, ITGA4 and ITGB1, or at least COL11A1, COL5A2, MMP2, MMP9, BMP1, ITGA4, ITGB1 and COL5A1, or at least COL11A1, COL5A2, MMP2, MMP9, BMP1, ITGA4, ITGB1, COL5A1 and TGFB1. In another particular embodiment, the nine genes are selected. In another embodiment the biomarkers for detecting the degradation of the ECM in a subject are the expression products of at least one gene disclosed in table ibis in addition to at least one gene disclosed in table 1 or any of their combinations as defined above.

It has been found that degradation of the ECM is related to cancer, and in particular, of malignant development of tumors and metastasis. It has also been found that the degradation of the ECM is closely related to the growth and risk for rupture of aneurysms. Thus, an additional embodiment of the invention refers to the method for detecting degradation of the ECM in a subject as defined above, wherein the degradation of the ECM is indicative of the patient suffering from cancer, aneurysm or both cancer and aneurysm.

Cancer

As shown in example 1, quite surprisingly, the inventors have found that some of the genes listed in table 1 are significantly up-regulated in peripheral blood of cancer patients when compared to a reference value, which allows for rapid and easy diagnosis of cancer. The inventors have shown that is possible to discriminate between patients with non-small cell lung cancer and controls (subjects without any malignancy) with a sensitivity of 0.98 (95% confidence intervals: 0.89-1.00, P<0.001) and a specificity of 1.00 (95% confidence intervals: 0.61-1.00, P<0.001). These results indicate that the method of the invention may accurately diagnose cancer from peripheral blood with high specificity and sensitivity.

The fingerprint for diagnosing cancer comprises the genes which are shown in table 4 and 4bis.

TABLE 4

Genetic fingerprint for diagnosing cancer.

| name | symbol | NCBI Reference Sequence |
| --- | --- | --- |
| collagen type XI alpha 1 chain | COL11A1 | NG_008033.1 |
| collagen type V alpha 2 chain | COL5A2 | NG_011799.2 |
| collagen type V alpha 1 chain | COL5A1 | NG_008030.1 |
| integrin subunit alpha 4 | ITGA4 | NG_050623.1 |
| integrin subunit beta 1 | ITGB1 | NG_029012.1 |
| matrix metallopeptidase 2 | MMP2 | NG_008989.1 |
| matrix metallopeptidase 9 | MMP9 | NG_011468.1 |
| bone morphogenetic protein 1 | BMP1 | NG_029659.1 |

TABLE 4bis

Genetic fingerprint for diagnosing cancer.

| name | symbol | NCBI Reference Sequence |
| --- | --- | --- |
| transforming growth factor beta-1 | TGFB1 | NG_013364.1 |
| integrin subunit alpha 3 | ITGA3 | NG_029107.2 |
| integrin subunit alpha 6 | ITGA6 | NG_008853.1 |
| tissue inhibitor of matrix metallopeptidase 1 | TIMP1 | NG_012533.1 |
| collagen type I alpha 1 chain | COL1A1 | NG_007400.1 |
| collagen type III alpha 1 chain | COL3A1 | NG_007404.1 |
| collagen type I alpha 2 chain | COL1A2 | NG_007405.1 |

Therefore, another aspect of the invention refers to an in vitro method for diagnosing cancer in a subject, the method comprising determining in an isolated sample from the subject the level of an expression product of at least one gene selected from the group of genes listed in table 4, wherein when the level of the expression product(s) is(are) higher than a reference value this is indicative that the subject suffers from cancer.

"Reference value" and "higher than a reference value" are understood as explained above. In a preferred embodiment of the aspects of the invention related to cancer the reference value is obtained from a subject or group of subjects that do not have any cancer malignancy. In some preferred embodiments of the aspects of the invention related to cancer, "higher than a reference value" is understood as the following fold increase in the level of expression (overexpression) of each of the gene expression products with respect to the reference value:

at least 5 fold overexpression with respect to the reference value for COL11A1,
at least 2 fold overexpression with respect to the reference value for COL5A2,
at least 2 fold overexpression with respect to the reference value for COL5A1,
at least 5 fold overexpression with respect to the reference value for MMP2,
at least 7 fold overexpression with respect to the reference value for MMP9,
at least 2 fold overexpression with respect to the reference value for BMP1,
at least 1 fold overexpression with respect to the reference value for ITGA4, or
at least 2 fold overexpression with respect to the reference value for ITGB1.

The inventors have also found that there is a direct correlation between the levels of the mRNA in peripheral blood of the genes disclosed in table 4 and the stage of the cancer.

Most types of cancer have 4 stages, numbered from I to IV. Stage I usually means that a cancer is relatively small in size and contained within the organ it started in. Stage II usually means that the tumor is larger than in stage I, but the cancer has not started to spread into the surrounding tissues. Sometimes stage II means that cancer cells have spread into lymph nodes close to the tumor. This depends on the particular type of cancer. Stage III usually means the cancer is larger and it may have started to spread into surrounding tissues and there are cancer cells in the lymph nodes in the area. Stage IV means the cancer has spread from where it started to another distant tissue or organ.

The correlation between overexpression of the genes in table 4 and cancer stage is shown in example 1. While all genes from table 4 are overexpressed measured as the level of mRNA when compared to the reference group, it may be observed that overexpression of the genes is lower, albeit statistically significant, in patients having non-small lung cancer in stage I, and steadily grows through stages II, III and IV. The inventors have demonstrated that patients with advanced metastatic non-small cell lung cancer (stages III and IV) can be differentially diagnosed from patients with early stage non-small cell lung cancer (stages I and II) with a sensitivity of 0.95 (95% confidence intervals: 0.78-0.99, P<0.001) and a specificity of 0.96 (95% confidence intervals: 0.80-0.99, P<0.001).

Thus the invention also refers to an in vitro method for the differential diagnosis of patients according to their cancer stage, the method comprising determining in an isolated sample from the subject the level of an expression product of at least one gene selected from the group of genes listed in table 4. Increasing levels of expression product(s) is(are) correlated with increasing cancer stage. Patients with cancers stage III or IV are often referred as patients having advanced cancer. In particular, when the expression product(s) has(have) the following level(s):

at least 10 fold overexpression with respect to the reference value for COL11A1,
at least 5 fold overexpression with respect to the reference value for COL5A2,
at least 5 fold overexpression with respect to the reference value for COL5A1,
at least 8 fold overexpression with respect to the reference value for MMP2,
at least 11 fold overexpression with respect to the reference value for MMP9,
at least 5 fold overexpression with respect to the reference value for BMP1,
at least 6 fold overexpression with respect to the reference value for ITGA4, or
at least 8 fold overexpression with respect to the reference value for ITGB1,
this is indicative that the subject suffers from metastatic cancer in stages III or IV (advanced cancer).

The method of the invention is also for in vitro differential diagnosis of patients with advanced cancer (stages III and IV) and patients with early stage cancer (stages I and II), wherein when the expression product(s) has(have) the level(s) as defined above, this is indicative that the patient has advanced cancer stage, while when the expression product(s) has(have) a level(s) below the thresholds defined above, this this is indicative that the patient has early cancer stage.

Stages III and IV in cancer are also frequently considered as implying a high risk of metastasis. "Metastasis" in the sense of the present invention is understood as usually in the art as the process by which cancer cells spread to new areas of the body different from the primary cancer site (often by way of the lymph system or bloodstream). Tumors formed from cells that have spread are called secondary tumors. The cancer may have spread to areas near the primary site (regional metastasis), or to parts of the body that are farther away (distant metastasis). The method of the invention provides a reliable test for identifying cancer patients at high risk to develop metastasis or at early stages of the metastatic process. This is a great advantage for the clinical management of cancer patients, who may receive the most appropriate therapy according to their progression and be subjected to a tight follow-up schedule if so needed when the risk of metastasis is high.

Thus, the present invention also provides a method for determining the risk of cancer metastasis in a subject, the method comprising determining in an isolated sample from the subject the level of an expression product of at least one gene selected from the group of genes listed in table 4. High levels of expression product(s) is(are) indicative of high risk of metastasis. In particular, when the expression product(s) has(have) the following level(s):

at least 10 fold overexpression with respect to the reference value for COL11A1, at least 5 fold overexpression with respect to the reference value for COL5A2, at least 5 fold overexpression with respect to the reference value for COL5A1, at least 8 fold overexpression with respect to the reference value for MMP2, at least 11 fold overexpression with respect to the reference value for MMP9, at least 5 fold overexpression with respect to the reference value for BMP1, at least 6 fold overexpression with respect to the reference value for ITGA4, or at least 8 fold overexpression with respect to the reference value for ITGB1, this is indicative that the subject has high risk of cancer metastasis.

According to all the above, categorization of cancer patients according to their cancer stage is thus possible by using the method of the invention. Therefore, another aspect of the invention refers to an in vitro method for categorizing cancer patients according to their cancer stage, said method comprising determining in an isolated sample from the subject the level of an expression product of at least one gene selected from the group consisting of the genes listed in table 4 and correlating said level of expression product with a cancer stage.

The present method may also provide early information on the risk of relapses in patients that have been treated for cancer and have overcome the illness. "Relapse" is, as understood generally in the art, deterioration in someone's state of health after a temporary improvement. This is very important in clinical terms since early detection and subsequent management of relapse in cancer patients may highly improve the prognosis of the patient suffering the relapse.

Thus another aspect of the invention refers to an in vitro method for detecting relapse in a subject that has been treated for cancer, the method comprising determining in an isolated sample from the subject the level of an expression product of at least one gene selected from the group consisting of the genes of table 4, wherein when the level of the expression product(s) is(are) higher than a reference value this is indicative that the patient is in high risk of suffering a relapse.

One further aspect of the invention refers to an in vitro method for prognosis of a cancer patient, the method comprising determining in an isolated sample from the patient the level of an expression product of at least one gene selected from the group consisting of the genes listed in table 4. High level of expression product(s) is(are) indicative of bad prognosis. In particular, when the expression product(s) has(have) the following level(s):

at least 10 fold overexpression with respect to the reference value for COL11A1, at least 5 fold overexpression with respect to the reference value for COL5A2, at least 5 fold overexpression with respect to the reference value for COL5A1, at least 8 fold overexpression with respect to the reference value for MMP2, at least 11 fold overexpression with respect to the reference value for MMP9, at least 5 fold overexpression with respect to the reference value for BMP1, at least 6 fold overexpression with respect to the reference value for ITGA4, or at least 8 fold overexpression with respect to the reference value for ITGB1, this is indicative of bad prognosis.

The present method is not restricted to a particular type of cancer. The overall mechanisms of cancer progression and spread over causing metastasis in relation to the degradation of the ECM are common to some extend to almost all types cancers. The changes in the expression levels of the genes, which are taking place in the tissue level, were clearly detected in the peripheral blood with a sensitivity of 98% and a specificity of 100% when comparing controls with non-small cell lung cancer patients and with a sensitivity of 95% and a specificity of 96% when comparing lung cancer patients at early stages (stages I and II) with patients at late metastatic stages (stages III and IV). Similar tissue expression patterns we have confirmed in female patients with breast cancer diagnosis. Therefore, because these detected changes in fact are reflecting the changes in the ECM, they can be used for the discrimination of patients with other types of cancer, in particular those which have the ability to metastasize through the degradation of the ECM.

In particular embodiments the cancer is non-small cell lung cancer, breast cancer, colon cancer, rectal cancer, small intestine cancer, prostate cancer, small cell lung cancer, mesothelioma, kidney cancer, pancreatic cancer, stomach cancer, esophageal cancer, laryngeal cancer, oropharyngeal cancer, liver cancer, bile duct cancer, gallbladder cancer, bladder cancer, thyroid cancer, endometrial cancer, ovarian cancer, vaginal cancer, urethral cancer, testicular cancer, bone cancer, brain cancer, skin cancer, melanoma, sarcoma, angiosarcoma, liposarcoma etc. In particular embodiments the cancer is non-small cell lung cancer or breast cancer, for example non-small cell lung cancer.

While providing for a reliable and early diagnosis of cancer, including categorization of patients with respect to the progression of their disease and metastasis, the present diagnosis method is useful to a clinician in the sense that the method enables him/her to take the most appropriate decisions to treat the patient. Since the anti-cancer treatment regimes may highly depend on the stage of cancer and, particularly, whether there is metastasis or high risk of metastasis, the clinician may, in view of the differential diagnosis performed as explained above, recommend the most appropriate (conservative or aggressive) anti-cancer therapy.

Thus, in another aspect, the invention is directed to an in vitro method for recommending an anti-cancer therapy in a subject, the method comprising: (a) diagnosing if the subject suffers from cancer or determining the bad prognosis of the subject suffering cancer by the methods as defined above, and (b) recommending an anti-cancer therapy if the subject is diagnosed of suffering from cancer or from bad prognosis of cancer. This aspect could also be contemplated as a method for treating a cancer patient comprising (a) diagnosing if the subject suffers from cancer or determining the bad prognosis of the subject suffering cancer by the methods as defined above, and (b) administering anti-cancer therapy to the patient if the subject is diagnosed of suffering from cancer or from bad prognosis of cancer. If the patient is not diagnosed with cancer the clinician may recommend follow-up of the subject.

In some embodiments, the method is for recommending a therapy for metastatic cancer in a subject when the diagnosis indicates that the subject has metastatic cancer.

Anti-cancer therapies include surgery, chemotherapy, radiation therapy, immunotherapy, targeted therapy and hormone therapy. Most cancer patients have a combination of treatments depending on the type of cancer and how advanced it is at the time of diagnosis. Preferably, the anti-cancer treatment is selected from the above mentioned options based on type and stage of cancer, the results of clinical trials as well as histopathologic findings. Therapeutic regimes for treating metastatic cancer depend on the type of primary cancer, the site of spread, treatment used in the past and the general health of the patient. In most cases, therapeutic regimes for treating metastatic cancer comprise a combination of at least two therapies selected from surgery, chemotherapy, radiation therapy, immunotherapy, targeted therapy and hormone therapy in their most aggressive forms. Although some types of metastatic cancer can be cured with current treatments, most cannot. In most metastatic cancers the goal of these treatments is to stop or slow the growth of the cancer or to relieve symptoms (palliative therapy), while in some cases, treatments for metastatic cancer may help prolong life. It is also important to mention that therapeutic interventions for metastatic cancers in most cases include chemotherapy and/or radiation therapy with significant side effects, which cannot be tolerated by a considerable number of patients until completion of the therapeutic cycles, highlighting thus, the need for early diagnosis even at the case of metastatic occurrence.

In addition, according to the present invention cancer patients who have received a specific treatment may be monitored in order to ensure the effectiveness of the therapeutic intervention or to warn early of relapse or the occurrence of metastatic disease. The present method allows for convenient follow-up and improved management of cancer patients, thus avoiding unnecessary suffering and/or minimizing side effects. A successful therapeutic intervention will, for example, result in expression levels of these genes that are close to controls and this effect should be maintained as long as there is no recurrence or metastatic disease.

Thus one further aspect of the invention provides an in vitro method for determining the response of a cancer patient to an anti-cancer therapy, the method comprising determining in an isolated sample from the patient the level of an expression product of at least one gene selected from the group consisting of the genes of table 4 and comparing said level of expression product with the level of expression product of the same gene(s) determined for the same patient before the start of the therapy or at an earlier phase of the therapy, wherein a decrease of the expression product of the gene(s) with respect to initiation of therapy or earlier phase of the therapy is indicative of a good response.

Another aspect may be defined as an in vitro method for recommending an alternative and/or complementary therapy in a cancer patient, the method comprising determining in an isolated sample from the patient the level of an expression product of at least one gene selected from the group consisting of the genes of table 4 and comparing said level of expression product with the level of expression product of the same gene(s) determined for the same patient before the start of the therapy or at an earlier phase of the therapy, wherein when the expression product of the gene(s) is increased with respect to the start of the therapy or earlier phase of the therapy, this is indicative of recommending alternative and/or complementary therapy. This may also be formulated as a method for treating a cancer patient who is not responding to anti-cancer therapy, the method comprising determining in an isolated sample from the patient the level of an expression product of at least one gene selected from the group consisting of the genes of table 4 and comparing said level of expression product with the level of expression product of the same gene(s) determined for the same patient before the start of the therapy or at an earlier phase of the therapy, and administering an alternative and/or complementary therapy when the expression product of the gene(s) is increased with respect to start of the therapy or earlier phase of the therapy. Sometimes the clinician may even recommend or administer an alternative and/or complementary therapy when the expression product of the gene(s) is unchanged with respect to start of the therapy or earlier phase of the therapy.

In all the above methods referred to cancer, the level of expression product of at least COL11A1 and/or COL5A2 is preferably determined. In particular embodiments, the methods comprise determining the level of an expression product of at least one gene selected from the group consisting of COL5A1, ITGA4, ITGB1, MMP2, MMP9 and BMP1, the at least one gene being determined optionally in combination with one or both of COL11A1 and COL5A2, wherein when the level of the expression product(s) is(are) higher than a reference value this is indicative that the subject suffers from cancer. Preferably the expression products of both COL11A1 and COL5A2 are determined. In other embodiments, the methods comprise determining the level of expression product of at least three, at least four, at least five, at least six, at least seven or at least eight of the genes disclosed in table 4. In a particular embodiment, the expression product of at least COL11A1, COL5A2, and COL5A1 is determined. In other particular embodiments the expression product of at least the following genes is determined: COL11A1, COL5A2, COL5A1 and MM2, or at least COL11A1, COL5A2, COL5A1, MMP2 and MMP9, or at least COL11A1, COL5A2, COL5A1, MMP2, MMP9 and BMP1, or at least COL11A1, COL5A2, COL5A1, MMP2, MMP9, BMP1 and ITGA4, or at least COL11A1, COL5A2, COL5A1, MMP2, MMP9, BMP1, ITGA4 and ITGB1. In another particular embodiment, expression product of the eight genes is determined. In other embodiments of the invention the level of expression product of at least one gene selected from the genes in table 4bis is additionally determined. In some embodiment the above methods referred to cancer comprise determining the level of expression product of at least one gene selected from the genes in table 4bis in addition to at least one gene disclosed in table 4 or any of their combinations as defined above.

The biological sample obtained from the patient may be, as already disclosed above, any tissue, or a bodily fluid such as blood, plasma, saliva, urine, cerebrospinal fluid, or semen, preferably peripheral blood. A diagnostic test based on samples of peripheral blood is quite simple, less invasive and cost-effective for a wide application in the general population. More specifically aged patients with limited access to tertiary diagnostic centers will be able to achieve diagnosis and monitoring with simple and cost-effective blood tests. It is well-established in the clinical setting to monitor the cancer patients after therapeutic intervention with computer tomography scans every six months during the first two years and then annually. Similarly, the diagnostic blood test of the invention carries a promising potential for a reliable monitoring of cancer patients following therapeutic interventions. Because the blood test is relatively more simple, convenient and cost-effective without the adverse effects of the radiation that the serial computer tomography scans are carrying could be used more frequently. The diagnostic test of the invention could be used every three months in order to detect earlier recurrences of malignancies and also prior the scanning of the patients with computer tomographies, in such a way that if they are showing low or normal levels of the expression levels of the genes that are related with malignancy and metastatic disease they could dictate the postpone of the computer tomography scanning for a future time point, when its contribution to the potential diagnosis of recurrence could be adequately justified.

The level of expression product of the genes is determined as disclosed above. In some embodiments the expression product is mRNA and is preferably determined by reverse transcription followed by real-time quantitative PCR. Amplification primers are derived from the transcript mRNA sequences of the genes disclosed in tables 4 and 4bis (as shown in table 2), and appropriate primers for amplifying the transcript sequences are provided in table 3. In other embodiments the expression product is the encoded protein(s) and is determined by mass spectrometry or immunochemistry as explained above.

Another aspect of the invention refers to use of means for determining the level of expression product of at least one gene selected from the group consisting of the genes of table 4 in the methods related to cancer as defined above. In a particular embodiment, the means are at least for determining the level of expression product of COL11A1 and/or COL5A2. In another particular embodiment, the means are for determining the level of expression product of at least one gene selected from the group consisting of COL5A1, ITGA4, ITGB1, WP2, MMP9 and BMP1, optionally in combination with one or both of COL11A1 and COL5A2. Preferably means are for determining the expression products of both COL11A1 and COL5A2. In particular embodiments the means are for determining the level of an expression product of at least three genes, at least four genes, at least five genes, at least six genes, at least seven genes or at least eight genes selected from the group of genes disclosed in table 4. In other particular embodiments, the means include means for determining the level of an expression product of at least the following genes: COL11A1, COL5A2 and COL5A1, or at least COL11A1, COL5A2, COL5A1 and MMP2, or at least COL11A1, COL5A2, COL5A1, MMP2 and MMP9, or at least COL11A1, COL5A2, COL5A1, MMP2, MMP9 and BMP1, or at least COL11A1, COL5A2, COL5A1, MMP2, MMP9, BMP1 and ITGA4, or at least COL11A1, COL5A2, COL5A1, MMP2, MMP9, BMP1, ITGA4 and ITGB1. In another embodiment the means are for determining the level of an expression product of all the genes disclosed in table 4. In another embodiment the means are for determining the level of an expression product of at least one gene disclosed in table 4bis in addition to at least one gene disclosed in table 4 or any of their combinations as defined above.

In particular embodiments the means are for determining mRNA. In one embodiment the means comprise amplification primers. In particular embodiments the primers are in each case those shown in table 3. In other embodiments the means are for determining proteins or fragments thereof. In particular embodiments, the means are antibodies or fragments thereof that specifically bind to the target protein(s).

In another embodiment the means form part of a kit. The kits of the invention may comprise said means for determining the level of an expression product and instructions for use in cancer diagnosis/prognosis/risk of metastasis/categorization according to stage as defined above. The instructions may include information regarding thresholds for determining cancer diagnosis/prognosis/risk of metastasis/categorization according to stage as defined above and/or reference values.

The invention also provides, in another aspect, for use of an expression product of at least one gene selected from the group consisting of the genes listed in table 4 as biomarker(s) for in vitro diagnosing cancer in a subject. The invention also refers use of said biomarkers for in vitro differential diagnosis of cancer patients according to their cancer stage. Some embodiments refer to use of said biomarkers for differential diagnosis of cancer patients having cancer in stages III or IV. Other embodiments refer to use of said biomarkers for differential diagnosis of patients with advanced cancer (stages III and IV) and patients with early stage cancer (stages I and II). Particular embodiments refer to the use of said biomarkers for diagnosing high risk of cancer metastasis in a subject. Another aspect provides for use of an expression product of at least one gene selected from the group consisting of genes of table 4 as biomarker(s) for diagnosing relapse in patients that have already undergone treatment intervention for cancer.

Another aspect of the invention provides for use of an expression product of at least one gene selected from the group consisting of the genes listed in table 4 as biomarker(s) for the in vitro prognosis of cancer in a subject. Another aspect provides for use of an expression product of at least one gene selected from the group consisting of genes of table 4 as biomarker(s) for recommending an anti-cancer therapy to a subject suffering from cancer. In one embodiment the use is for recommending a therapy for metastatic cancer to a subject having high risk of metastasis.

One further aspect provides for use of an expression product of a gene selected from the group consisting of the genes listed in table 4 as biomarker(s) for determining the response of a cancer patient to a specific anti-cancer therapy.

In some embodiments of the above aspects at least COL11A1 and/or COL5A2 are the selected biomarkers. Another embodiment provides for the use of an expression product of at least one gene selected from the group consisting of COL5A1, ITGA4, ITGB1, MMP2, MMP9 and BMP1, optionally in combination with one or both of COL11A1 and COL5A2, as the in vitro biomarkers. Preferably, both COL11A1 and COL5A2 are among the selected biomarkers. In other embodiments, the selected biomarkers are the expression products of at least three, at least four, at least five, at least six, at least seven or at least eight of the genes disclosed in table 4. In a particular embodiment, the expression product of at least COL11A1, COL5A2 and COL5A1 is selected. In other particular embodiments the expression product of at least the following genes is selected: at least COL11A1, COL5A2, COL5A1 and MMP2, or at least COL11A1, COL5A2, COL5A1, MMP2 and MMP9, or at least COL11A1, COL5A2, COL5A1, MMP2, MMP9 and BMP1, or at least COL11A1, COL5A2, COL5A1, MMP2, MMP9, BMP1 and ITGA4, or at least COL11A1, COL5A2, COL5A1, MMP2, MMP9, BMP1, ITGA4 and ITGB1. In another particular embodiment, expression product of the eight genes is selected. In other embodiments the biomarkers are the expression products of at least one gene disclosed in table 4bis in addition to at least one gene disclosed in table 4 or any of their combinations as defined above.

Aneurysm

It has also been found that the level of expression of some of the genes disclosed in table 1 is closely related to aneurysms. The genetic fingerprint for diagnosing aneurysms comprises the genes which are shown in tables 5 and 5bis.

As shown in example 2, quite surprisingly, the inventors have found that some of those genes are significantly up-regulated in peripheral blood of patients that suffer from a thoracic aortic aneurysm when compared to a reference value, which allows for rapid and easy diagnosis of this condition. The inventors have also shown that it is possible to discriminate between patients that have a thoracic aortic aneurysm and controls (subjects without any thoracic aortic aneurysm or cancer) with a sensitivity of 0.95 (95% confidence intervals: 0.89-1.00, P<0.001) and a specificity of 0.92 (95% confidence intervals: 0.78-1.00, P<0.001). These results indicate that the method of the invention may accurately diagnose aneurysms from peripheral blood sample.

TABLE 5

Genetic fingerprint for diagnosing aneurysm.

| name | symbol | reference |
|---|---|---|
| collagen type XI alpha 1 chain | COL11A1 | NG_008033.1 |
| collagen type V alpha 2 chain | COL5A2 | NG_011799.2 |
| transforming growth factor beta-1 | TGFB1 | NG_013364.1 |
| integrin subunit alpha 4 | ITGA4 | NG_050623.1 |
| integrin subunit beta 1 | ITGB1 | NG_029012.1 |
| matrix metallopeptidase 2 | MMP2 | NG_008989.1 |
| matrix metallopeptidase 9 | MMP9 | NG_011468.1 |
| bone morphogenetic protein 1 | BMP1 | NG_029659.1 |

TABLE 5bis

Genetic fingerprint for diagnosing aneurysm.

| name | symbol | NCBI Reference Sequence |
|---|---|---|
| collagen type V alpha 1 chain | COL5A1 | NG_008030.1 |
| integrin subunit alpha 3 | ITGA3 | NG_029107.2 |
| integrin subunit alpha 6 | ITGA6 | NG_008853.1 |
| tissue inhibitor of matrix metallopeptidase 1 | TIMP1 | NG_012533.1 |
| collagen type I alpha 1 chain | COL1A1 | NG_007400.1 |
| collagen type III alpha 1 chain | COL3A1 | NG_007404.1 |
| collagen type I alpha 2 chain | COL1A2 | NG_007405.1 |

Therefore, another aspect of the invention refers to an in vitro method for diagnosing an aneurysm in a subject, the method comprising determining in an isolated sample from the subject the level of an expression product of at least one gene selected from the group consisting of the genes disclosed in table 5, wherein when the level of the expression product(s) is(are) higher than a reference value this is indicative that the subject suffers from an aneurysm.

"Reference value" and "higher than a reference value" are understood as explained above. In a preferred embodiment of the aspects of the invention related to aneurysm the reference value is obtained from a subject or group of subjects that do not have any aneurysms. In some preferred embodiments of the aspects of the invention related to aneurysm, "higher than a reference value" is understood as the following fold increase in the level of expression (overexpression) of each of the gene expression products with respect to the reference value:

at least 5 fold overexpression with respect to the reference value for COL11A1, at least 1.5 fold overexpression with respect to the reference value for COL5A2, at least 3 fold overexpression with respect to the reference value for TGFB1, at least 3 fold overexpression with respect to the reference value for MMP2, at least 2.5 fold overexpression with respect to the reference value for MMP9, at least 5 fold overexpression with respect to the reference value for BMP1, at least 1.5 fold overexpression with respect to the reference value for ITGA4, or at least 3 fold overexpression with respect to the reference value for ITGB1.

Moreover, as indicated by the results of example 2, the inventors have found that there is a direct correlation between the levels of the mRNA in peripheral blood of the genes shown in table 5 and the size of the thoracic aortic aneurysm.

Aneurysms are commonly divided according to their size and symptomatology. An aneurysm of any blood vessel in the body, it is defined in general, as an increased outer blood vessel diameter of more than 50% of the normal diameter of a healthy individual, based on gender and age normal values. The normal diameter of the adult thoracic aorta is between 2 and 3 cm. A thoracic aorta with a diameter of 4.5 cm (50% increase as compared to 3 cm) is considered as an aortic aneurysm. It has been estimated that the risk for rupture or dissection of a thoracic aortic aneurysm it is considerably higher when the aortic diameter is above 5 cm and the risk of rupture is getting even higher in larger diameters. A thoracic aortic aneurysm with a diameter between 5 to 6 cm should be considered for intervention from clinical point of view. In larger thoracic aortic aneurysms (6-7 cm in diameter) or even in very large thoracic aortic aneurysms (diameter >7 cm) the need for intervention is considered urgent and emergent respectively.

The correlation between overexpression of the genes in table 5 and the size of aortic aneurysm is shown in example 2. It can be observed that overexpression of the genes measured as the expression level of mRNA, is lower, albeit statistically significant, in patients having smaller size aortic aneurysms (i.e. aortic diameter 5-6 cm vs. aortic diameter 6-7 cm vs. aortic diameter >7 cm). In contrast, the overexpression of the genes is significantly elevated in patients with very large aortic aneurysms (outer aortic diameter above 7 cm). The inventors have demonstrated that with the method of the invention patients with relatively large aortic aneurysms (aortic diameter equal or above 6 cm) can be differentially diagnosed from patients with relatively small size aortic aneurysms (aortic diameter between 4.5 and 6 cm) with a sensitivity of 0.95 (95% confidence intervals: 0.86-1.00, P<0.001) and a specificity of 0.86 (95% confidence intervals: 0.71-1.00, P<0.001).

In one embodiment the method of the invention is for differential diagnosis of patients according to size of the aneurysm, the method comprising determining in an isolated sample from the subject the level of an expression product of at least one gene selected from the group of genes listed in table 5. Increasing levels of expression product(s) is(are) correlated with increasing size of the aneurysm. In another embodiment the method is for differential diagnosis of patients having a large size aneurysm. In another embodiment the method is for differential diagnosis of patients with large aneurysm and patients with small size aneurysm. In particular, when the expression product(s) has(have) the following level(s):

at least 15 fold overexpression with respect to the reference value for COL11A1, at least 5 fold overexpression with respect to the reference value for COL5A2, at least 10 fold overexpression with respect to the reference value for TGFB1, at least 10 fold overexpression with respect to the reference value for MMP2, at least 12 fold overexpression with respect to the reference value for MMP9, at least 10 fold overexpression with respect to the reference value for BMP1, at least 5 fold overexpression with respect to the reference value for ITGA4, or at least 8 fold overexpression with respect to the reference value for ITGB1, this is indicative that the patient has a large aneurysm, for example, a large aortic aneurysm (equal or above 6 cm diameter). When the level of expression product(s) is higher than the reference value but below these thresholds, this is indicative that the patient's aneurysm is relatively small size aneurysm, in particular, for aortic aneurysms, below 6 cm in diameter.

Aneurysms, in particular large diameter aneurysms, are considered at risk of rupture. Rupture of the vessel, such as the aorta, results in massive internal bleeding and, unless treated immediately, shock and death can occur. Surgery is recommended to avoid the rupture if the size of the aneurysm is reaching specific diameters (i.e. above 5 cm in diameter in the ascending thoracic aorta or above 6 cm in the descending thoracic aorta) and/or it is growing rapidly (more than 0.5 cm per year). Up to now, the most cost-efficient screening test, to determine if a patient has an aneurysm at risk for rupture, is performed by computer tomography study. The method of the invention constitutes a reliable, convenient and more cost-effective test for identifying patients at risk for rupture. Appropriate medical intervention, such as surgery, may be recommended by the clinician in view of the expression pattern of the genes of table 5 after a simple blood sampling. Additionally, the patient may be subjected to a tight follow-up schedule if so needed. Thus, the invention also refers to an in vitro method for diagnosing the risk of rupture of an aneurysm in a subject, the method comprising determining in an isolated sample from the subject the level of an expression product of at least one gene selected from the group consisting of the genes of table 5. High level of expression product(s) is indicative of risk for rupture. In particular when the expression product(s) has(have) the following level(s):

at least 15 fold overexpression with respect to the reference value for COL11A1, at least 5 fold overexpression with respect to the reference value for COL5A2, at least 10 fold overexpression with respect to the reference value for TGFB1, at least 10 fold overexpression with respect to the reference value for MMP2, at least 12 fold overexpression with respect to the reference value for MMP9, at least 10 fold overexpression with respect to the reference value for BMP1, at least 5 fold overexpression with respect to the reference value for ITGA4, or at least 8 fold overexpression with respect to the reference value for ITGB1, this is indicative of high risk for rupture of the aneurysm.

The overexpression of the genes of table 5 is directly proportional to the size of the aneurysm. Consequently, categorization of aneurysm patients according to the size of the aneurysms, or according to having high risk or low risk for rupture, is possible by using the method of the invention. Therefore, another aspect of the invention refers to an in vitro method for categorizing aneurysm patients according to the size of the aneurysm, the method comprising determining in an isolated sample from the subject the level of an expression product of at least one gene selected from the group consisting of the genes of table 5 and correlating said level(s) with the size of aneurysm and the risk for rupture. Appropriate thresholds for such categorization are as defined above.

One further aspect of the invention refers to an in vitro method for the prognosis of an aneurysm in a patient, the method comprising determining in an isolated sample from the patient the level of an expression product of at least one gene selected from the genes of table 5, wherein the level of expression product is directly correlated with bad prognosis. Thus, a high level of expression product(s) is indicative of bad prognosis. In particular, when the expression product(s) has(have) the level(s) defined above for the risk of rupture, this is indicative of bad prognosis.

The present method is not restricted to a particular type of aneurysm. The overall mechanisms of aneurysm progression in relation to the degradation of the ECM is common to all aneurysms. In particular embodiments the aneurysm is selected from aortic aneurysm, which can be either thoracic (ascending thoracic or arch or descending thoracic aortic aneurysm) or abdominal or thoracoabdominal aortic aneurysm. Other vessels experiencing aneurysmal disease with poor prognosis in advanced stages are the cerebral arterial vessels, the iliac arteries and the subclavian arteries. In a preferred embodiment, the aneurysm is thoracic aortic aneurysm.

While providing for a reliable and early diagnosis of aneurysm, including categorization of patients with respect to the progression of their disease and the risk of rupture, the present diagnosis method is useful to a clinician in the sense that the method enables him/her to take the most appropriate decisions to treat the patient. Since the treatment regime may depend on the size of the aneurysm, and particularly, whether there is a risk for rupture, the clinician may, in view of the differential diagnosis performed as explained above, recommend the most appropriate therapy, including surgical intervention. Recommendation for surgical intervention could be also advised even in small diameter aneurysms in case they are expressing high levels of the molecular indicators proposed in this invention, given the fact that, although rare, there are small aneurysms prone to rupture, and there are sporadic cases of ruptured aneurysms with relatively small diameters. The biomarkers of the invention are overall a good indicator of prognosis regarding the risk for rupture of the aneurysm. Thus, in sporadic cases, a small aneurysm may result in high levels of expression products of the disclosed markers, which would be nevertheless indicative of bad prognosis and high risk for rupture, thus providing very useful information for the clinical management of the particular patient.

Thus, in another aspect, the invention is directed to an in vitro method for recommending a therapeutic regime for aneurysm in a subject comprising: (a) diagnosing if the subject suffers from aneurysm or determining bad prognosis by the methods as defined above, and (b) recommending a therapeutic regime for aneurysm if the subject is diagnosed of suffering from an aneurysm or determined to have bad prognosis. This aspect could also be contemplated as a method for treating a patient having an aneurysm comprising (a) diagnosing if the subject suffers from aneurysm or determining bad prognosis by the methods as defined above, and (b) administering a therapeutic regime for treating aneurysm to the patient if the method indicates that the subject has an aneurysm or bad prognosis. If the patient is not diagnosed with aneurysm the clinician may recommend follow-up of the subject.

Therapeutic regimes for treating aneurysm include surgical replacement of the aneurysm by a synthetic graft or endovascular approach and stent grafting in an attempt to isolate the aneurysmal part of the vessel from the circulation of the blood. Preferably, the regime for treating aneurysm is selected based on the anatomy and the location of the aneurysm, (there are certain anatomical restrictions that totally exclude the possibility of the endovascular approach) as well as, the age and the general condition of the patient.

In some embodiments, the method is for recommending an appropriate therapeutic regime for patients at high risk for rupture of the blood vessel when the diagnosis indicates that such risk exists. Usually the appropriate therapy in these cases is a surgical intervention, either open surgery or endovascular therapy with stent graft implantation with minimal invasive approach. Other adjuncts of pharmacologic intervention, but not therapeutic treatments, include the administration of statins, beta-blockers and aggressive anti-hypertensive agents.

In addition, according to the present invention patients having an aneurysm who have received a specific treatment may be monitored in order to ensure the effectiveness of the therapeutic intervention or to warn early of the risk for rupture of the affected blood vessel. The present method allows for easy follow-up and improved management of patients with aneurysms, thus avoiding unnecessary suffering and/or minimizing side effects. For example, a successful therapeutic intervention will result in expression levels of these genes that are close to controls.

Thus one further aspect of the invention provides an in vitro method for determining the response of a patient that suffers from an aneurysm to therapeutical regime for aneurysm, the method comprising determining in an isolated sample from the patient the level of an expression product of at least one gene selected from table 5 and comparing said level of expression product with the level of expression product of the same gene(s) determined for the same patient before the start of the therapy or at an earlier phase of the therapy, wherein a decrease of the expression product of the gene(s) with respect to start the therapy or earlier phase of the therapy is indicative of a good response.

Another aspect may be defined as an in vitro method for recommending an alternative and/or complementary therapeutic regime for a patient having an aneurysm, the method comprising determining in an isolated sample from the patient the level of an expression product of at least one gene selected from table 5 and comparing said level of expression product with the level of expression product of the same gene(s) determined for the same patient before the start of the therapy or at an earlier phase of the therapy, wherein an increase of the expression product of the gene(s) with respect to start the therapy or earlier phase of the therapy indicates that an alternative and/or complementary therapeutic regime is needed. This may also be formulated as a method for treating a patient having an aneurysm that is not responding to a therapeutic regime for aneurysm, especially in the case of endovascular approach where the aneurysm remains in the body, said method comprising determining in an isolated sample from the patient the level of an expression product of at least one gene selected from table 5 and comparing said level of expression product with the level of expression product of the same gene(s) determined for the same patient before the start of the therapy or at an earlier phase of the therapy, and administering alternative and/or complementary therapeutic regime for aneurysm when the expression product of the gene(s) is increased with respect to start the therapy or earlier phase of the therapy. Sometimes the clinician may even recommend or administer an alternative and/or complementary therapy when the expression product of the gene(s) is unchanged with respect to start of the therapy or earlier phase of the therapy.

The present method may also provide early information on the risk of relapses in patients that have been treated for aneurysm. A successful therapeutic intervention will result in expression levels of the genes that are close to controls. However, one patient who has developed an aortic aneurysm remains at risk to develop another aortic aneurysm at another site of the native aorta. Early detection and subsequent management of relapse may highly improve the prognosis of the patient suffering from aneurysm.

Thus another aspect of the invention refers to an in vitro method for detecting relapse in a subject that has been treated for aneurysm, the method comprising determining in an isolated sample from the subject the level of an expression product of at least one gene selected from the group consisting of the genes of table 5, wherein when the level of the expression product(s) is(are) higher than a reference value this is indicative that the subject is in high risk of suffering a relapse.

In all the above methods referred to aneurysm, the level of expression product of at least COL11A1 and/or COL5A2 is preferably determined. In particular embodiments, the methods comprise determining the level of an expression product of at least one gene selected from the group consisting of TGFB1, ITGA4, ITGB1, MMP2, MMP9 and BMP1, the at least one gene being determined optionally in combination with one or both of COL11A1 and COL5A2, wherein when the level of the expression product(s) is(are) higher than a reference value this is indicative that the subject suffers from aneurysm. Preferably the expression products of both COL11A1 and COL5A2 are determined. In other embodiments, the methods comprise determining the level of expression product of at least three, at least four, at least five, at least six, at least seven or at least eight of the genes disclosed in table 5. In a particular embodiment, the expression product of at least COL11A1, COL5A2, and MMP2 is determined. In other particular embodiments the expression product of at least the following genes is determined: COL11A1, COL5A2, MMP2 and MMP9, or at least COL11A1, COL5A2, MMP2, MMP9 and BMP1, or at least COL11A1, COL5A2, MMP2, MMP9, BMP1 and ITGA4, or at least COL11A1, COL5A2, MMP2, MMP9, BMP1, ITGA4 and ITGB1, or at least COL11A1, COL5A2, MMP2, MMP9, BMP1, ITGA4, ITGB1 and TGFB1. In another particular embodiment, expression product of the eight genes is determined. In other embodiments of the invention the level of expression product of at least one gene selected from the genes in table 5bis is additionally determined. In some embodiment the above methods referred to aneurysm comprise determining the level of expression product of at least one gene selected from the genes in table 5bis in addition to at least one gene disclosed in table 5 or any of their combinations as defined above.

The biological sample obtained from the patient may be, as already disclosed above, any tissue, or a bodily fluid such as blood, plasma, saliva, urine, cerebrospinal fluid, or semen. Preferably, the sample is peripheral blood.

It is well-established in the clinical setting to monitor the patients with aneurysms, for example, aortic aneurysms with computer tomography scans every six months prior to surgery (until the aortic diameter reaches the point of the surgical intervention), and also, every six months postoperatively after surgical intervention during the first year and then annually. Similarly, the diagnostic blood test of the invention carries a promising potential for a reliable monitoring of patients with aneurysm, for example, aortic aneurysms following therapeutic interventions including also the cases of endovascular stenting interventions. In the case of the endovascular interventions, there are many cases in which the aortic aneurysm continues to expand in diameter, despite its isolation from the circulation and the effect of the blood pressure, resulting in devastating complications such as stent migration. The blood diagnostic test of the invention has the potential to be a good prognostic indicator for the complications of endovascular procedures as well. Because the blood test is relatively more convenient and cost-effective without the adverse effects of the radiation that the serial computer tomography scans are carrying could be used more frequently. The diagnostic blood test of the invention could be used every three months in order to detect earlier the changes in aortic diameter and also prior the scanning of the patients with computer tomographies, in such a way that if they are showing low or normal levels of the expression levels of the genes that are related with aortic aneurysm expansion, they could dictate the postpone of the computer tomography scanning for a future time point, when its contribution to the potential diagnosis of a larger aortic aneurysm could be adequately justified.

The level of expression product of the genes is determined as disclosed above. In some embodiments the expression product is mRNA and is preferably determined by reverse transcription followed by real-time quantitative PCR. Amplification primers are derived from the transcript mRNA sequences of the genes disclosed in tables 5 and 5bis (as shown in table 2), and appropriate primers for amplifying the transcript sequences are provided in table 3. In other embodiments the expression product is the encoded protein(s) and is determined by mass spectrometry or immunochemistry as explained above.

Another aspect of the invention refers to use of means for determining the level of expression product of at least one gene selected from the group consisting of the genes of table 5 in the methods related to aneurysm as defined above. In a particular embodiment, the means are at least for determining the level of expression product of COL11A1 and/or COL5A2. In another particular embodiment, the means are for determining the level of expression product of at least one gene selected from the group consisting of TGFB1, ITGA4, ITGB1, MMP2, MMP9 and BMP1, optionally in combination with one or both of COL11A1 and COL5A2. Preferably means are for determining the expression products of both COL11A1 and COL5A2. In particular embodiments the means are for determining the level of an expression product of at least three genes, at least four genes, at least five genes, at least six genes, at least seven genes or at least eight genes selected from the group of genes disclosed in table 5. In a particular embodiment, the expression product of at least COL11A1, COL5A2, and MMP2 is selected. In other particular embodiments the expression product of at least the following genes is selected: COL11A1, COL5A2, MMP2 and MMP9, or at least COL11A1, COL5A2, MMP2, MMP9 and BMP1, or at least COL11A1, COL5A2, MMP2, MMP9, BMP1 and ITGA4, or at least COL11A1, COL5A2, MMP2, MMP9, BMP1, ITGA4 and ITGB1, or at least COL11A1, COL5A2, MMP2, MMP9, BMP1, ITGA4, ITGB1 and TGFB1. In another embodiment the means are for determining the level of an expression product of all the genes disclosed in table 5. In another embodiment the means are for determining the level of an expression product of at least one gene disclosed in table 5bis in addition to at least one gene disclosed in table 5 or any of their combinations as defined above.

In particular embodiments the means are for determining mRNA. In one embodiment the means comprise amplification primers. In particular embodiments the primers are in each case those shown in table 3. In another embodiment the means form part of a kit. The kits of the invention may comprise said means for determining the level of an expression product and instructions for use in aneurysm diagnosis/prognosis/risk for rupture/categorization according to size as defined above. The instructions may include information regarding thresholds for determining aneurysm diagnosis/prognosis/risk for rupture/categorization according to size as defined above and/or reference values.

The invention also provides, in another aspect, for use of an expression product of at least one gene selected from the group consisting of the genes of table 5 as biomarker(s) for in vitro diagnosing an aneurysm in a subject. In some embodiments said biomarkers are for the differential diagnosis of the patients according to the size of their aneurysm. In other embodiments said biomarkers are for differential diagnosis of patients having large aneurysm, for example, in the case of aortic aneurysm, having a size above 6 cm. In another embodiment the method is for diagnosis of patients having an aneurysm at risk for rupture. In another embodiment the method is for differential diagnosis of patients having large aneurysm and patients with small or medium size aneurysm, for example, for aortic aneurysms, differential diagnosis of patients having aneurysm of diameter larger than 6 cm and patients with aneurysm of diameter below 6 cm.

Another aspect of the invention provides for use of an expression product of at least one gene selected from the group consisting of the genes of table 5 as biomarker(s) for the in vitro prognosis of patients with an aneurysm. Another aspect of the invention provides for use of an expression product of at least one gene selected from the group consisting of the genes of table 5 as biomarker(s) for determining the response of patient suffering from an aneurysm to a therapeutic regime for aneurysm.

In some embodiments of the above aspects at least COL11A1 and/or COL5A2 are the selected biomarkers. Another embodiment provides for the use of an expression product of at least one gene selected from the group consisting of TGFB1, ITGA4, ITGB1, MMP2, MMP9 and BMP1, optionally in combination with one or both of COL11A1 and COL5A2, as the in vitro biomarkers. Preferably, both COL11A1 and COL5A2 are among the selected biomarkers. In other embodiments, the selected biomarkers are the expression products of at least three, at least four, at least five, at least six, at least seven or at least eight of the genes disclosed in table 5. In a particular embodiment, the expression product of at least COL11A1, COL5A2, and MMP2 is selected. In other particular embodiments the expression product of at least the following genes is selected: COL11A1, COL5A2, MMP2 and MMP9, or at least COL11A1, COL5A2, MMP2, MMP9 and BMP1, or at least COL11A1, COL5A2, MMP2, MMP9, BMP1 and ITGA4, or at least COL11A1, COL5A2, MMP2, MMP9, BMP1, ITGA4 and ITGB1, or at least COL11A1, COL5A2, MMP2, MMP9, BMP1, ITGA4, ITGB1 and TGFB1. In another particular embodiment, expression product of the eight genes is selected. In other embodiments the biomarkers are the expression products of at least one gene disclosed in table 5bis in addition to at least one gene disclosed in table 5 or any of their combinations as defined above.

The in vitro methods of the invention provide diagnostic prognostic and/or response to treatment (monitoring) information. In one embodiment, the methods of the invention further comprise the steps of (i) collecting the diagnostic, prognostic, and/or response to treatment (monitoring) information, and (ii) saving the information in a data carrier.

In the sense of the invention a "data carrier" is to be understood as any means, such as paper, that contain meaningful information data for the diagnosis and/or prognosis of degradation of the ECM, cancer or aneurysm in a subject. Such means may be considered as a carrier. The carrier may also be any entity or device capable of carrying the prognosis data. For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal, which may be conveyed via electrical or optical cable or by radio or other means. When the diagnosis/prognosis/response to treatment data are embodied in a signal that may be conveyed directly by a cable or other device or means, the carrier may be constituted by such cable or other device or means. Other carriers relate to USB devices and computer archives. Examples of suitable data carrier are paper, CDs, USB, computer archives in PCs, or sound registration with the same information.

Finally, another aspect of present invention provides an algorithm for carrying out any of the methods of diagnosis, prognosis and/or response to treatment as defined in the above aspects. In the sense of the invention, the term "algorithm" is also synonymous of panel or decision diagrams, predictors and combinatory of data to correctly categorize an individual sample.

According to aspects and embodiments of the invention, diagnosis, prognosis and/or response to treatment of ECM degradation, cancer or aneurysm can be performed using a mathematical algorithm that assesses a detectable level of biomolecules, proteins, fragment of proteins, antibodies, and/or mRNA, comprising one or more of the biomarkers as defined above, either in conjunction with or independent of other clinical parameters, to correctly categorize an individual sample as originating from a healthy patient, a patient with degraded ECM, cancer (including the particular cancer stage and risk of metastasis), or aneurysms (including size of the aneurysm and risk of rupture).

The classification algorithm may be as simple as determining whether or not the amount of a specific biomarker or subset of biomarkers measured are above or below a particular threshold (reference value). When multiple biomarkers are used, the classification algorithm may be a linear regression formula. Alternatively, the classification algorithm may be the product of any of a number of learning algorithms. In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen. This algorithm is used as diagnostic and/or prognostic method, and it is in particular part of the kits for carrying out the methods disclosed in former aspects.

Throughout the description and claims the word "comprise" and variations of the word, are not intended to exclude other technical features, additives, components, or steps. Furthermore, the word "comprise" encompasses the case of "consisting of". All terms as used herein in this application, unless otherwise stated, shall be understood in their ordinary meaning as known in the art. Other more specific definitions for certain terms as used in the present application are as set forth above and are intended to apply uniformly through-out the specification and claims unless an otherwise expressly set out definition provides a broader definition.

Additional objects, advantages and features of the invention will become apparent to those skilled in the art upon examination of the description or may be learned by practice of the invention. The following examples and drawings are provided by way of illustration, and they are not intended to be limited of the present invention. Furthermore, the present invention covers all possible combinations of particular and preferred embodiments described herein.

EXAMPLES

Example 1

Expression Pattern in Cancer Patients

Figure 1:
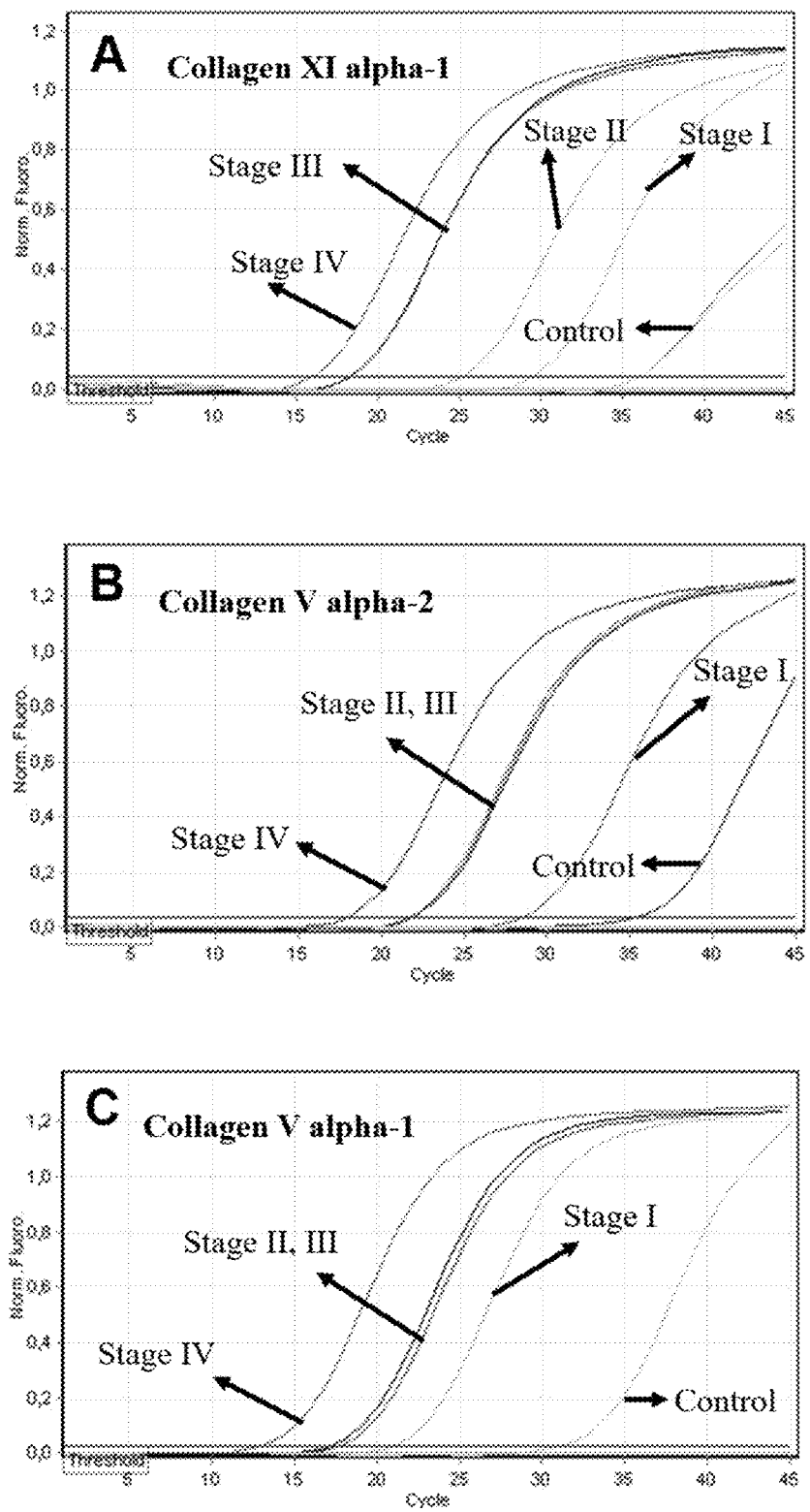
FIG. 1. Real-time quantitative RT-PCR reactions in cancer patients. Panels A to F show real-time quantitative amplification curves for Collagen XI alpha-1, Collagen V alpha-2, Collagen V alpha-1, Collagen I alpha-1, Collagen I alpha-2 and Collagen III alpha-1.
Figure 1:
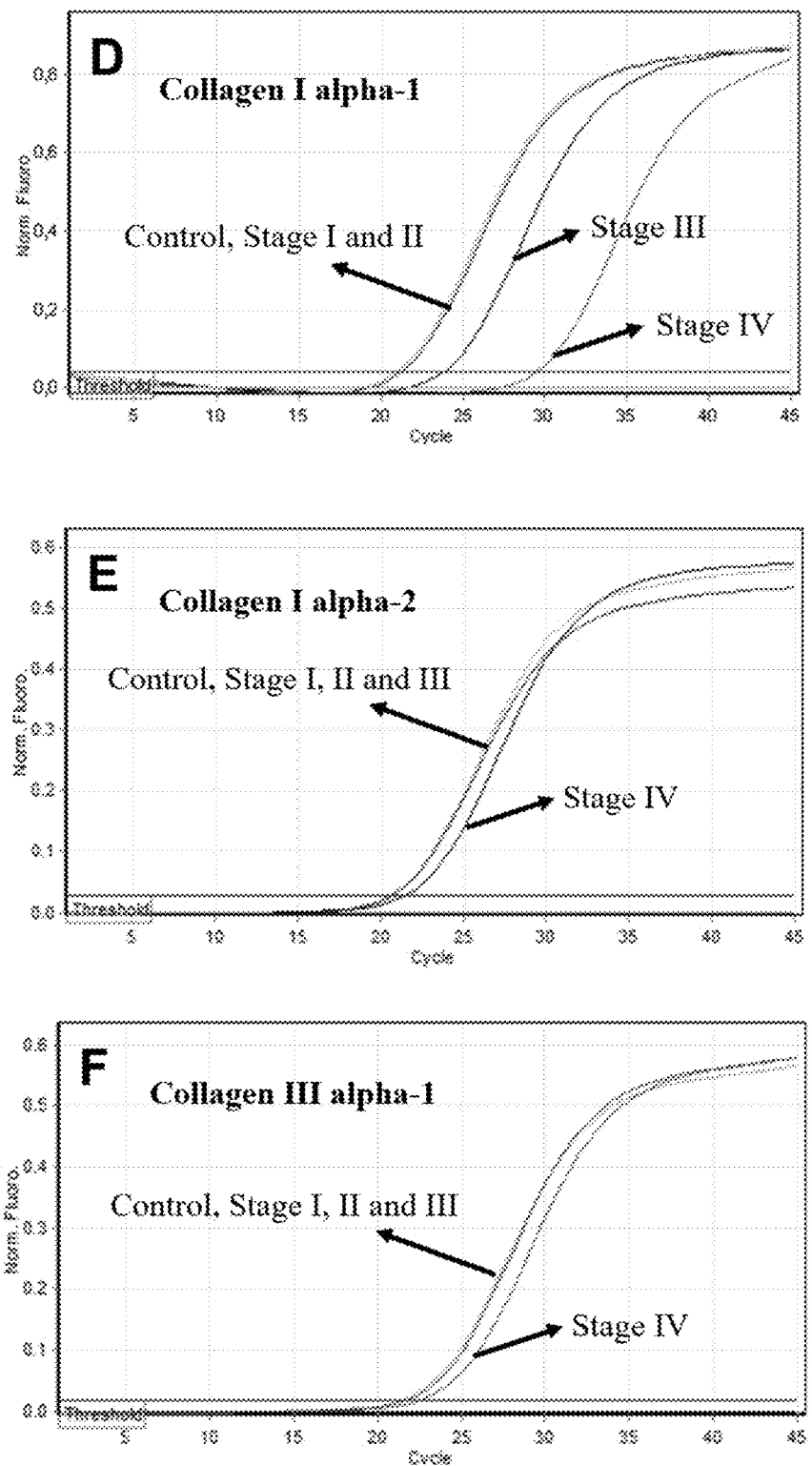

Methods: Total RNA was extracted from peripheral blood samples from patients with non-small cell lung cancer (total 46 patients: 13 patients stage I, 11 patients stage II, 13 patients stage III and 9 patients stage IV) and from patients without any malignancy (controls, n=6) as confirmed by computer tomography scans.

DNA was removed by an in-column recombinant DNase treatment. Total RNA was eluted in RNase-free water and stored at −80° C. until further use. RNA concentration was determined by the Quant-iT RNA Assay kit in the Qubit 1.0 Fluorometer (Invitrogen/Thermo Fisher, USA) that employs a dye specific for RNA and not for DNA. All RNAs were of adequate quantity.

cDNA was synthesized from 1 μg of total RNA and random hexamers and in a 20 μL total volume, according to the RT2 First Strand Kit (Qiagen, Germany) in thermal cycler Primus 25 (MWG-Biotech, Germany). The RT$^2$ First Strand Kit includes a proprietary genomic DNA elimination step to remove any residual contamination in RNA samples before reverse transcription, thereby eliminating false positive signals. An RNA negative control (blank) was also used. cDNA concentration was determined by the Quant-iT DNA Assay kit in the Qubit 1.0 Fluorometer (Invitrogen/Thermo Fisher, USA) that employs a dye specific for DNA and not for RNA. The cDNA samples were then stored at −20° C., until real-time quantitative PCR analysis.

In order to study the mRNA expression levels of COL11A/(all variants), COL5A2, COL5A1 (all variants), TGFB1, ITGA4 (all variants), ITGB1 (all variants), MMP2 (all variants), MMP9, BMP1 (all variants), ITGA3, ITGA6 (all variants), TIMP1, COL1A1, COL3A1 and COL1A2 a real-time RT-qPCR assay was validated in Rotor-Gene Q MDX (Qiagen, Germany) real-time thermal cycler in a total volume of 20 μL by using the appropriate RT2 qPCR Primer Assays (Qiagen, Germany) and the RT2 SYBR Green Mastermix (Qiagen, Germany). All transcription products (variants) were determined for each of the genes. Primers were those disclosed in table 3 above. As a reference gene, the beta-actin was used. In order to perform the amplification, manufacturer's instructions were followed.

All products were checked for size and purity by electrophoresis on 2% w/v agarose gels and through melting point analysis. Within every run, each cDNA sample was amplified for one gene at the time. Also for our lab internal quality control, a random cDNA sample was chosen to be included in all runs. Identification of the studied genes is as follows:
 1. COL11A1 [Homo sapiens (human)], herein also termed
    Collagen XI alpha-1
    Gene ID: 1301
    Location: 1p21.1
    Exon count: 71
 2. COL5A2 [Homo sapiens (human)], herein also termed
    Collagen V alpha-2
    Gene ID: 1290
    Location: 2q32.2
    Exon count: 55
 3. COL5A1 [Homo sapiens (human)], herein also termed
    Collagen V alpha-1
    Gene ID: 1289
    Location: 9q34.3
    Exon count: 68
 4. COL3A1 [Homo sapiens (human)], herein also termed
    Collagen III alpha-1
    Gene ID: 1281
    Location: 2q32.2
    Exon count: 51
 5. COL1A1 [Homo sapiens (human)], also called herein
    as Collagen I alpha-1
    Gene ID: 1277
    Location: 17q21.33
    Exon count: 51
 6. COL1A2 [Homo sapiens (human)], herein also termed
    Collagen I alpha-2
    Gene ID: 1278
    Location: 7q21.3
    Exon count: 52
 7. ITGA3 [Homo sapiens (human)], herein also termed
    integrin receptor subunit alpha-3
    Gene ID: 3675
    Location: 17q21.33
    Exon count: 26
 8. ITGA4 [Homo sapiens (human)], herein also termed
    integrin receptor subunit alpha-4
    Gene ID: 3676
    Location: 2q31.3
    Exon count: 29
 9. ITGA6 [Homo sapiens (human)], herein also termed
    integrin receptor subunit alpha-6
    Gene ID: 3655
    Location: 2q31.1
    Exon count: 28
 10. ITGB1 [Homo sapiens (human)], herein also termed
    integrin receptor subunit beta-1
    Gene ID: 3688
    Location: 10p11.22
    Exon count: 18
 11. MMP2 [Homo sapiens (human)], herein also termed
    integrin receptor subunit beta-1matrix metallopeptidase 2
    Gene ID: 4313
    Location: 16q12.2
    Exon count: 17
 12. MMP9 [Homo sapiens (human)], herein also termed
    matrix metallopeptidase 9
    Gene ID: 4318
    Location: 20q13.12
    Exon count: 13
 13. TIMP1 [Homo sapiens (human)], herein also termed
    TIMP metallopeptidase inhibitor 1
    Gene ID: 7076
    Location: Xp11.3
    Exon count: 6
 14. BMP1 [Homo sapiens (human)], herein also termed
    bone morphogenetic protein 1
    Gene ID: 649
    Location: 8p21.3
    Exon count: 25

15. TGFB1 [Homo sapiens (human)], herein also termed transforming growth factor beta 1
   Gene ID: 7040
   Location: 19q13.2
   Exon count: 7
16. ACTB [Homo sapiens (human)], herein also termed actin beta
   Gene ID: 60
   Location: 7p22.1
   Exon count: 6
   The NCBI Reference Sequence for ACTB gene is NG 007992.1 (NG 007992.1 for its transcript)

In order to prepare calibrators (standards) for the beta-actin gene assay, several PCR products were united and then purified by the PureLink PCR Purification Kit (Invitrogen/Thermo Fisher) followed by measuring the concentration by the Quant-iT dsDNA Broad range Assay kit in the Qubit 1.0 Fluorometer (Invitrogen/Thermo Fisher, USA). The copies/µL were calculated as described previously (Kroupis C. et al, *Clin Biochem.* 2005, vol. 38, issue 1, p. 50-57). The highly concentrated calibrator was serially diluted and standard curves were obtained for both genes. As method of relative quantification, the $2^{-\Delta\Delta C_t}$ of Livak and Schmittgen (supra) was used (RQ=$2^{-\Delta\Delta C_t}$, wherein RQ is the mRNA expression).

Statistical methods: Sensitivity and specificity of qRT-PCR for combination of genes were calculated with 95% confidence intervals. Sensitivity/specificity results were measured as up-regulated transcript biomarkers within the group of patients with non-small cell lung cancer (n=46, sensitivity) and down-regulated transcript biomarkers within control patients (n=6, specificity). In addition, sensitivity/specificity results were measured as up-regulated transcript biomarkers within the subgroup of patients with advanced metastatic stages of non-small cell lung cancer (n=22, patients in stages III and IV—sensitivity) and down-regulated (or less up-regulated as compared with controls) transcript biomarkers within the subgroup of patients with early stages of non-small cell lung cancer (n=24, patients in stages I and II—specificity). P values were given by Fisher's exact tests comparing the proportions between the compared subgroups.

Results:

FIG. 1 shows representative real-time RT-PCR curves from various types of collagen in patients with non-small cell lung cancer. It is clearly shown that there were higher levels of mRNA expression of collagen types XI alpha-1, V alpha-2 and V alpha-1 in patients with non-small cell lung cancer as compared to controls. It is also shown that the levels of expression of these minor fibril-forming collagens were even more overexpressed in advanced and metastatic stages of non-small cell lung cancer (Stages III and IV). Table 6 shows the fold change expression pattern versus the reference group (non-cancer patients).

TABLE 6

Fold change expression pattern for various types of collagen in patients with non-small cell lung cancer versus the reference group (non-cancer patients)

| | Fold change vs. Control | | | | |
|---|---|---|---|---|---|
| | Controls (reference) | Stage I | Stage II | Stage III | Stage IV |
| Collagen XI alpha-1 | 1.000 | 4.931 | 8.853 | 14.081 | 20.821 |
| Collagen V alpha-2 | 1.000 | 1.879 | 2.946 | 5.364 | 7.833 |
| Collagen V alpha-1 | 1.000 | 1.537 | 2.479 | 4.756 | 6.038 |
| Collagen I alpha-1 | 1.000 | 0.976 | 0.954 | 0.795 | 0.613 |
| Collagen I alpha-2 | 1.000 | 0.985 | 0.981 | 0.953 | 0.919 |
| Collagen III alpha-1 | 1.000 | 1.023 | 0.984 | 0.968 | 0.852 |

Figure 2:
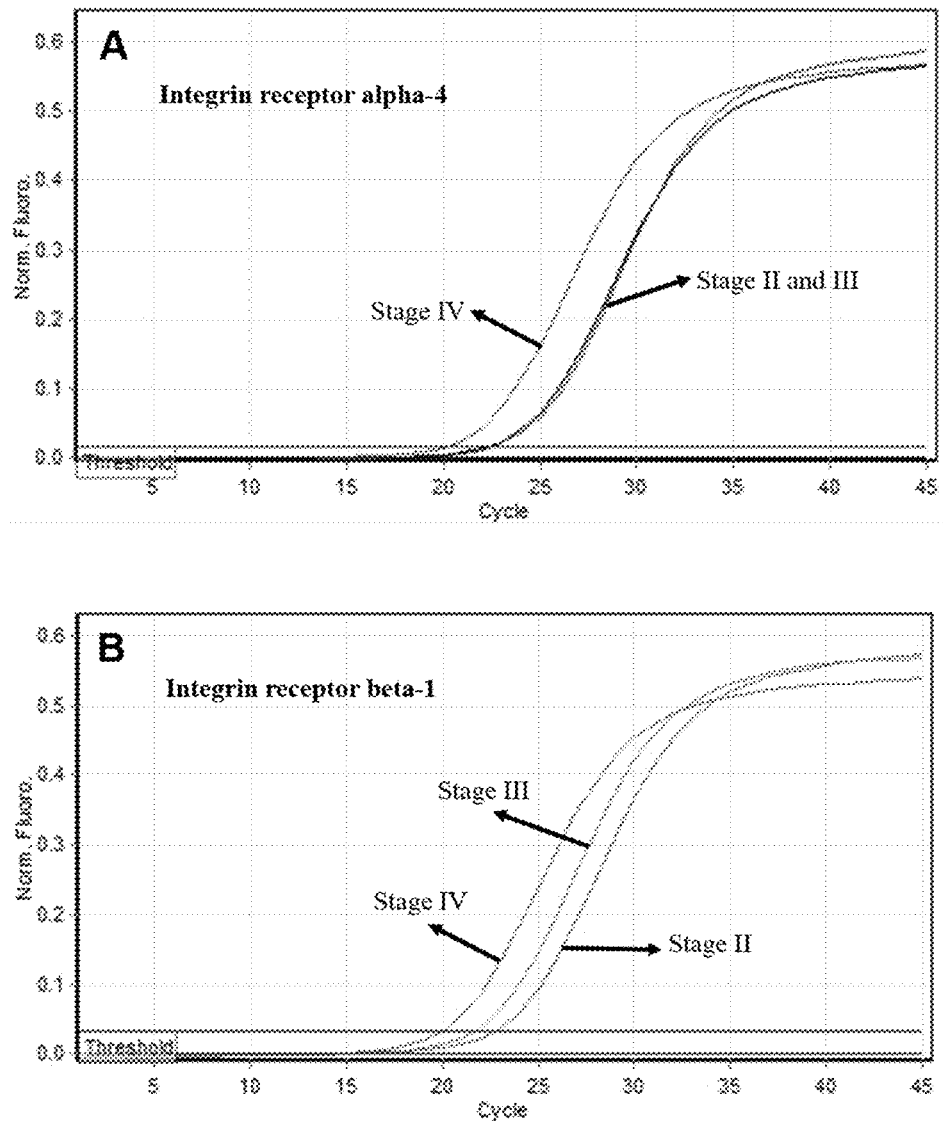
FIG. 2. Real-time quantitative RT-PCR reactions in cancer patients. Panels A to D show real-time quantitative amplification curves for Integrin receptor alpha-4, Integrin receptor beta-1, Integrin receptor alpha-3 and Integrin receptor alpha-6.
Figure 2:
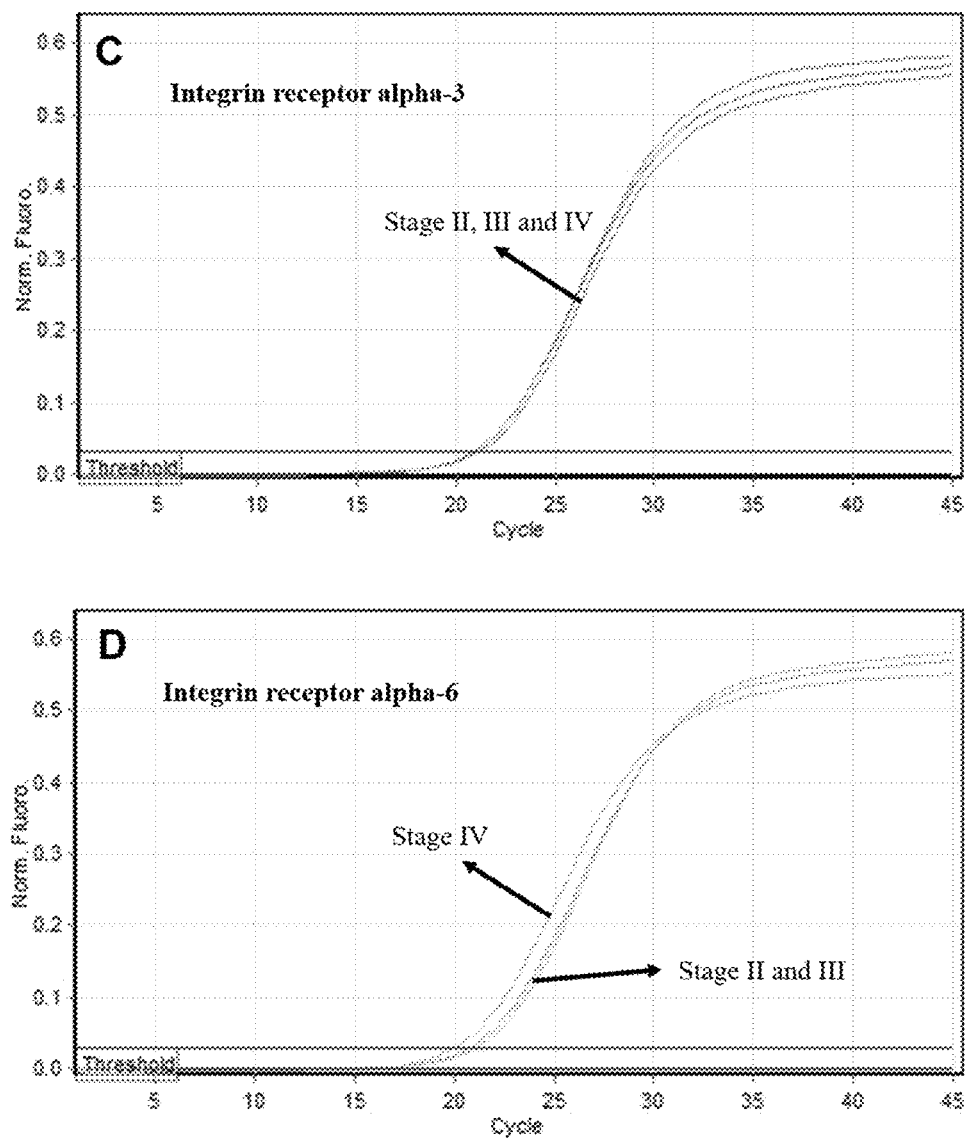

FIG. 2 shows representative real-time RT-PCR curves from various types of integrin receptors in patients with non-small cell lung cancer. It is clearly shown that there were higher levels of mRNA expression of integrin receptor alpha-4, beta-1, alpha-3 and alpha-6 in patients with non-small cell lung cancer as compared to controls. It is of note that the levels of expression of these Integrin receptors were higher in stage II and even more overexpressed in advanced and metastatic stages of non-small cell lung cancer (Stages III and IV). Table 7 shows the fold change expression pattern versus the reference group (non-cancer patients).

TABLE 7

Fold change expression pattern for various types of integrin receptors in patients with non-small cell lung cancer versus the reference group (non-cancer patients)

| | Fold change vs. Control | | | | |
|---|---|---|---|---|---|
| | Controls (reference) | Stage I | Stage II | Stage III | Stage IV |
| Integrin receptor alpha-4 | 1.000 | 1.023 | 5.553 | 6.534 | 13.012 |
| Integrin receptor beta-1 | 1.000 | 1.056 | 4.375 | 8.123 | 14.032 |
| Integrin receptor alpha-3 | 1.000 | 0.995 | 5.123 | 6.835 | 7.905 |
| Integrin receptor alpha-6 | 1.000 | 1.103 | 3.133 | 3.965 | 5.018 |

Figure 3:
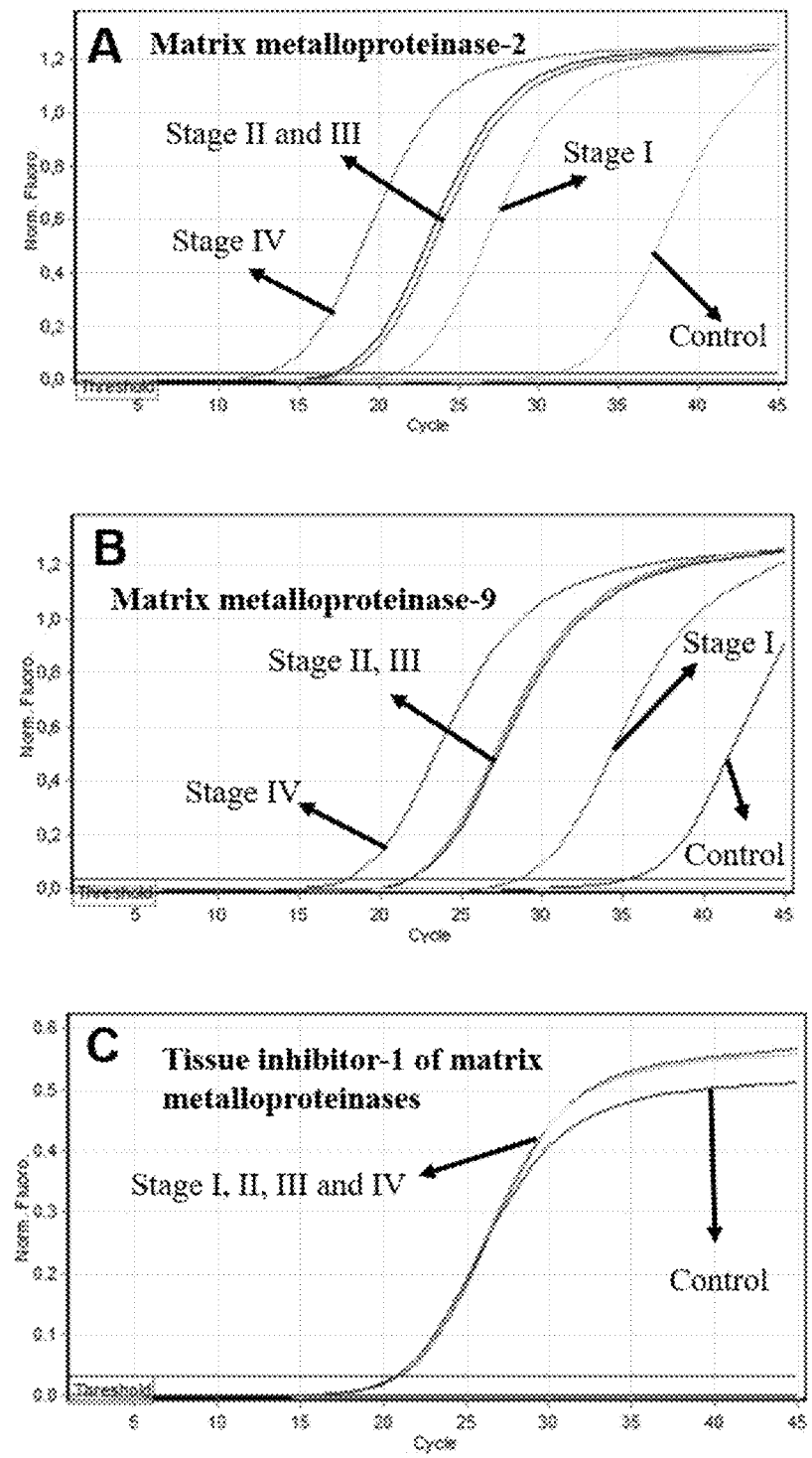
FIG. 3. Real-time quantitative RT-PCR reactions in cancer patients. Panels A to F show real-time quantitative amplification curves for Matrix metalloproteinase-2, Matrix metalloproteinase-9, Tissue inhibitor-1 of matrix metalloproteinases, Bone morphogenetic protein-1, Transforming growth factor beta-1 and Beta-actin.
Figure 3:
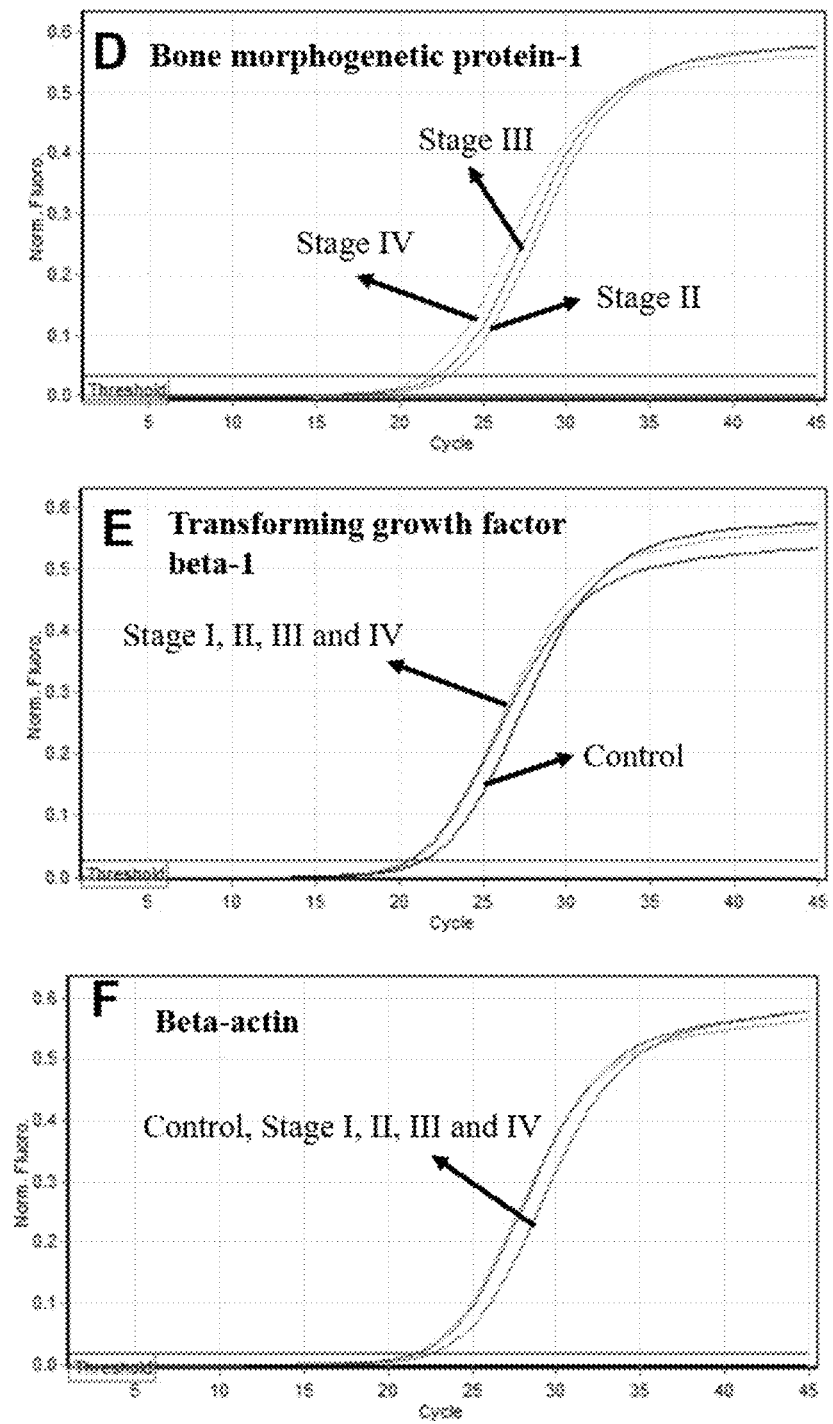

FIG. 3 shows representative real-time RT-PCR curves from matrix metalloproteinase-2, matrix metalloproteinase-9, tissue inhibitor-1 of matrix metalloproteinases, bone morphogenetic protein-1, transforming growth factor beta-1 and the reference gene of beta-actin in patients with non-small cell lung cancer. It is clearly shown that there were higher levels of mRNA expression of matrix metalloproteinase-2, matrix metalloproteinase-9, tissue inhibitor-1 of matrix metalloproteinases, bone morphogenetic protein-1, transforming growth factor beta-1 in patients with non-small cell lung cancer as compared to controls. It is also shown that the levels of expression of these mRNAs which are controlling the remodeling of the ECM were even more overexpressed in advanced and metastatic stages of non-small cell lung cancer (Stages III and IV). There were no changes in the expression levels of beta-actin among controls and different stages of non-small cell lung cancer patients. Table 8 shows the fold change expression pattern versus the reference group (non-cancer patients).

TABLE 8

Fold change expression pattern for various types of matrix metalloproteinases, bone morphogenetic protein-1, transforming growth factor beta-1 and the reference gene of beta-actin in patients with non-small cell lung cancer versus the reference group (non-cancer patients)

| | Fold change vs. Control | | | | |
|---|---|---|---|---|---|
| | Controls (reference) | Stage I | Stage II | Stage III | Stage IV |
| Matrix metalloproteinase-2 | 1.000 | 4.253 | 7.934 | 8.531 | 18.111 |
| Matrix metalloproteinase-9 | 1.000 | 6.771 | 11.195 | 12.259 | 19.321 |
| Tissue inhibitor-1 of matrix metalloproteinases | 1.000 | 1.830 | 1.982 | 2.003 | 2.200 |
| Bone morphogenetic protein-1 | 1.000 | 1.203 | 3.541 | 5.190 | 8.019 |
| Transforming growth factor beta-1 | 1.000 | 2.185 | 2.344 | 2.687 | 3.135 |
| Beta-actin | 1.000 | 1.013 | 0.994 | 0.981 | 1.098 |

All the products of the RT-PCR reactions were tested in agarose electrophoresis gel. All amplified products were represented by a single product at the expected molecular weight position. Further DNA sequencing analysis confirmed the expected sequences of the amplified PCR products.

In conclusion, it was found that the expression pattern of the genes collagen XI alpha-1, collagen V alpha-2, collagen V alpha-1, integrin receptor alpha-4, integrin receptor beta-1, matrix metalloproteinase-2, matrix metalloproteinase-9 and bone morphogenetic protein-1 provides reliable diagnostic information for cancer, in this case in particular, non-small cell lung cancer, in peripheral blood. There also exists a correlation between overexpression of these genes and cancer stage. This set of genes can adequately analyze the novel molecular mechanism which controls the remodeling/degradation of the ECM as described in above. More specifically, by using these 8 core genes it was possible to discriminate between patients with non-small cell lung cancer and controls with a sensitivity of 0.98 (95% confidence intervals: 0.89-1.00, P<0.001) and a specificity of 1.00 (95% confidence intervals: 0.61-1.00, P<0.001). Finally, the expression pattern of the 8 genes could discriminate between patients with advanced metastatic non-small cell lung cancer (stages III and IV) and patients with early stages non-small cell lung cancer (stages I and II) with a sensitivity of 0.95 (95% confidence intervals: 0.78-0.99, P<0.001) and a specificity of 0.96 (95% confidence intervals: 0.80-0.99, P<0.001).

The set of genes not only showed high sensitivity and specificity in discriminating between control and cancer patients and between cancer patients at early stages versus late metastatic stages, but in addition, it was possible to quantify between early and metastatic stages. More specifically, as it can be derived from the tables 6-8 and the FIGS. 1-3 it was possible to provide fold changes in the expression levels for the genes for quantification purposes between early and metastatic stages (table 9).

TABLE 9

Quantification of early and advanced (metastatic stages) of patients with non-small cell lung cancer based on the fold change versus controls in the expression levels (mRNA) of the genes in the peripheral blood.

| Gene | Early stages of cancer | Advanced (metastatic) stages of cancer |
|---|---|---|
| Collagen XI alpha-1 | >5 fold change | >10 fold change |
| Collagen V alpha-2 | >2 fold change | >5 fold change |
| Collagen V alpha-1 | >2 fold change | >5 fold change |
| Matrix metalloproteinase-2 | >5 fold change | >8 fold change |
| Matrix metalloproteinase-9 | >7 fold change | >11 fold change |
| Bone morphogenetic protein-1 | >2 fold change | >5 fold change |
| Integrin receptor alpha-4 | >1 fold change | >6 fold change |
| Integrin receptor beta-1 | >2 fold change | >8 fold change |

The panel of genes is the reflection of the remodeling of the ECM, which is essential in the monitoring and follow-up of patients especially after treatment intervention. A successful therapeutic intervention will result in expression levels of these genes that are close to controls. In the above experimental measurements, as presented in detail, it was found that the levels of minor fibril-forming collagens as well as the levels of the genes that are involved in the degradation of the ECM in patients without cancer (confirmed by computer tomography scans), are expressed in significantly lower levels in the peripheral blood. Although the above experiments were done in patients with non-small cell lung cancer, similar expression patterns we have confirmed in female patients with breast cancer diagnosis. Therefore, because these detected changes in fact are reflecting the changes in the ECM, they can be potentially used for the discrimination of patients with other types of cancer, which have the ability to metastasize through the degradation of the ECM.

Example 2

Expression Pattern in Aneurysm Patients

Methods: Total RNA was extracted from peripheral blood samples from patients with thoracic aortic aneurysms, namely in the ascending thoracic aorta (total 42 patients: 21 patients with thoracic aortic aneurysms with aortic diameter between 5 and 6 cm, 13 patients with thoracic aortic aneurysms with aortic diameter between 6 and 7 cm and 8 patients with thoracic aortic aneurysms with aortic diameter more than 7 cm) and from patients without aortic aneurysm (controls, n=13) as confirmed by computer tomography scans.

Figure 4:
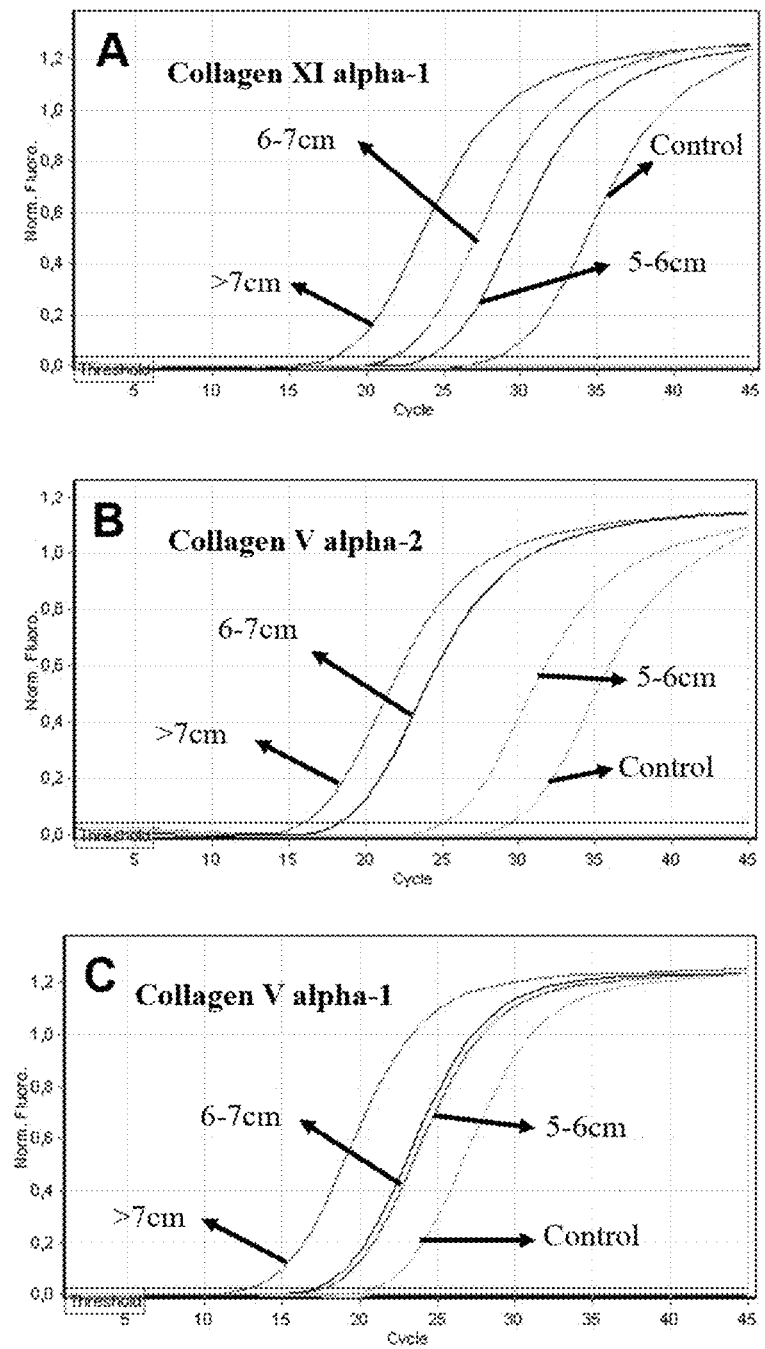
FIG. 4. Real-time quantitative RT-PCR reactions in aneurysm patients. Panels A to F show real-time quantitative amplification curves for Collagen XI alpha-1, Collagen V alpha-2, Collagen V alpha-1, Collagen I alpha-1, Collagen I alpha-2 and Collagen III alpha-1.
Figure 4:
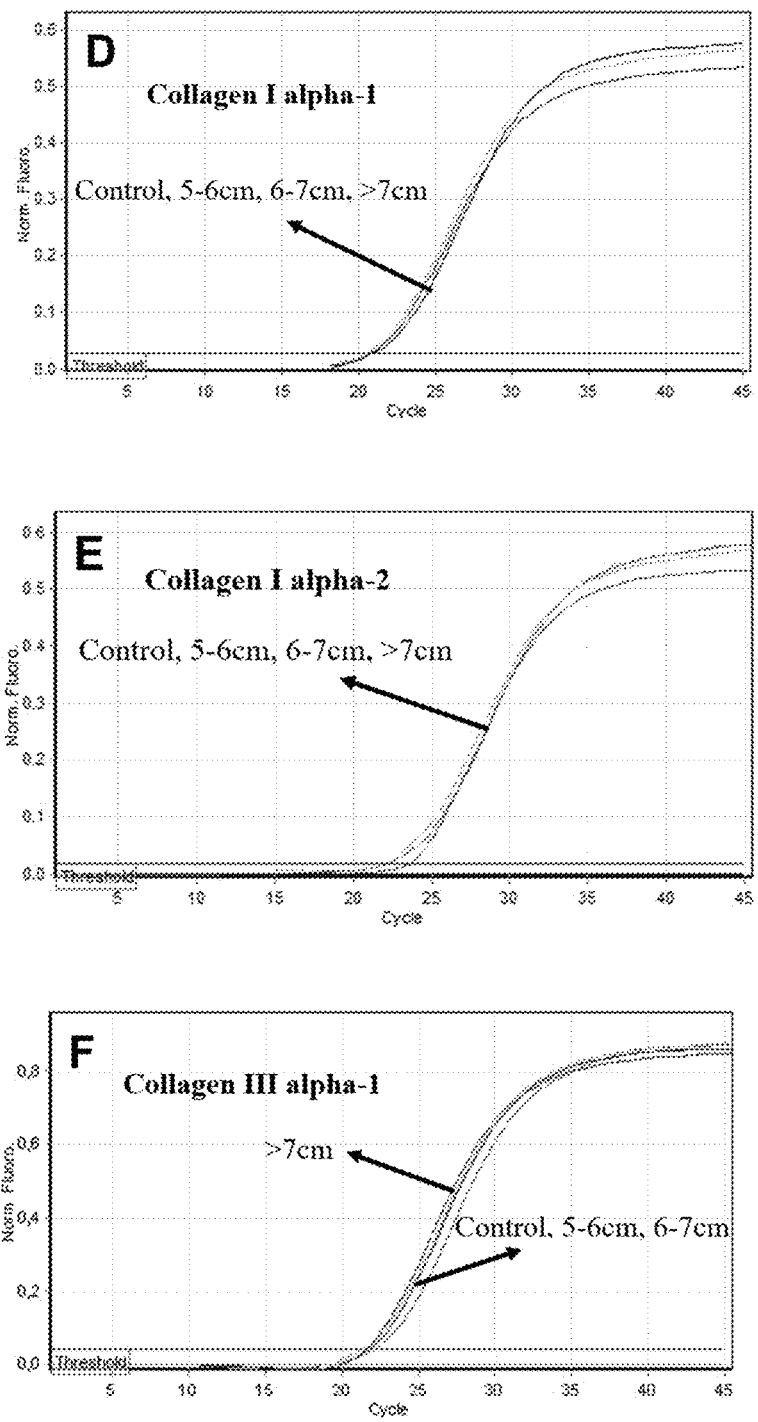

The methodology was the same as in example 1.
Results:

FIG. 4 shows representative real-time RT-PCR curves from various types of collagen in controls and in patients with small (aortic diameter 5-6 cm), medium (aortic diameter 6-7 cm) and large size thoracic aortic aneurysms (aortic diameter >7 cm). It is clearly shown that there were higher levels of mRNA expression of collagen types XI alpha-1, V alpha-2 and V alpha-1 in patients with thoracic aortic aneurysms as compared to controls. It is also shown that the levels of expression of these minor fibril-forming collagens are even more overexpressed in large size thoracic aortic aneurysms (aortic diameter >7 cm). Table 10 shows the fold change expression pattern versus the reference group (patients with normal diameter thoracic aorta, which is ranging between 2.5 and 3.0 cm).

TABLE 10

Fold change expression pattern for various types of collagen in patients with thoracic aortic aneurysms versus the reference group (patients with normal diameter thoracic aorta)

| | Fold change vs. Control | | | |
|---|---|---|---|---|
| | Controls (reference) | Aneurysm 5-6 cm | Aneurysm 6-7 cm | Aneurysm >7 cm |
| Collagen XI alpha-1 | 1.000 | 5.238 | 9.513 | 16.182 |
| Collagen V alpha-2 | 1.000 | 1.918 | 2.335 | 5.058 |
| Collagen V alpha-1 | 1.000 | 1.832 | 3.583 | 5.585 |
| Collagen I alpha-1 | 1.000 | 0.955 | 0.933 | 0.985 |
| Collagen I alpha-2 | 1.000 | 0.980 | 0.988 | 0.933 |
| Collagen III alpha-1 | 1.000 | 0.982 | 0.953 | 0.851 |

Figure 5:
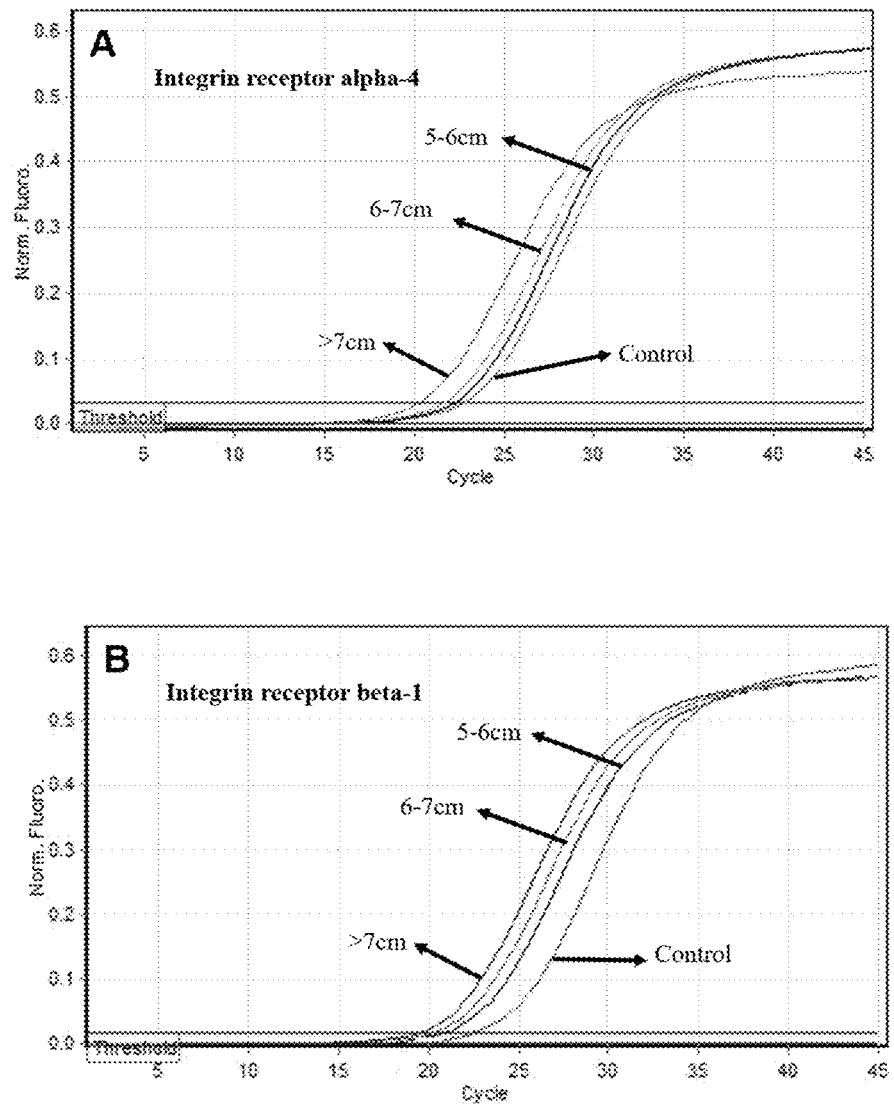
FIG. 5. Real-time quantitative RT-PCR reactions in aneurysm patients. Panels A to D show real-time quantitative amplification curves for Integrin receptor subunit alpha-4, Integrin receptor subunit beta-1, Integrin receptor subunit alpha-3 and Integrin receptor subunit alpha-6.
Figure 5:
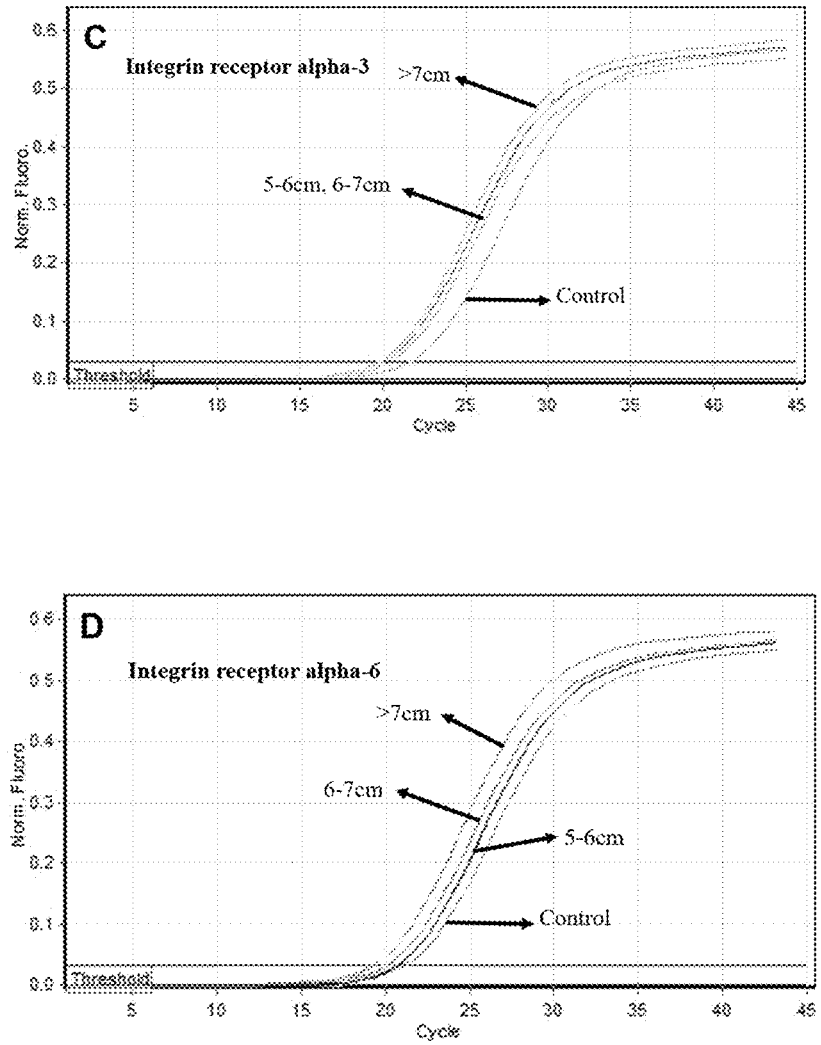

FIG. 5 shows representative real-time RT-PCR curves from various types of integrin receptors in patients with thoracic aortic aneurysms. It is clearly shown that there were higher levels of mRNA expression of integrin receptor subunit alpha-4, beta-1, alpha-3 and alpha-6 in patients with thoracic aortic aneurysms as compared to controls. It is of note that the increased levels of expression of these Integrin subunit receptors were shown in relatively small size aneurysms (aortic diameter 5-6 cm) and were even more overexpressed in larger size thoracic aortic aneurysms (aortic diameter 6-7 cm and >7 cm). Table 11 shows the fold change expression pattern versus the reference group (patients with normal diameter thoracic aorta).

TABLE 11

Fold change expression pattern for various types of integrin receptors in patients with thoracic aortic aneurysms versus the reference group (patients with normal diameter thoracic aorta)

| | Fold change vs. Control | | | |
|---|---|---|---|---|
| | Controls (reference) | Aneurysm 5-6 cm | Aneurysm 6-7 cm | Aneurysm >7 cm |
| Integrin receptor alpha-4 | 1.000 | 1.883 | 3.521 | 5.538 |
| Integrin receptor beta-1 | 1.000 | 3.588 | 5.852 | 8.222 |
| Integrin receptor alpha-3 | 1.000 | 3.385 | 3.880 | 5.001 |
| Integrin receptor alpha-6 | 1.000 | 1.805 | 2.832 | 4.350 |

Figure 6:
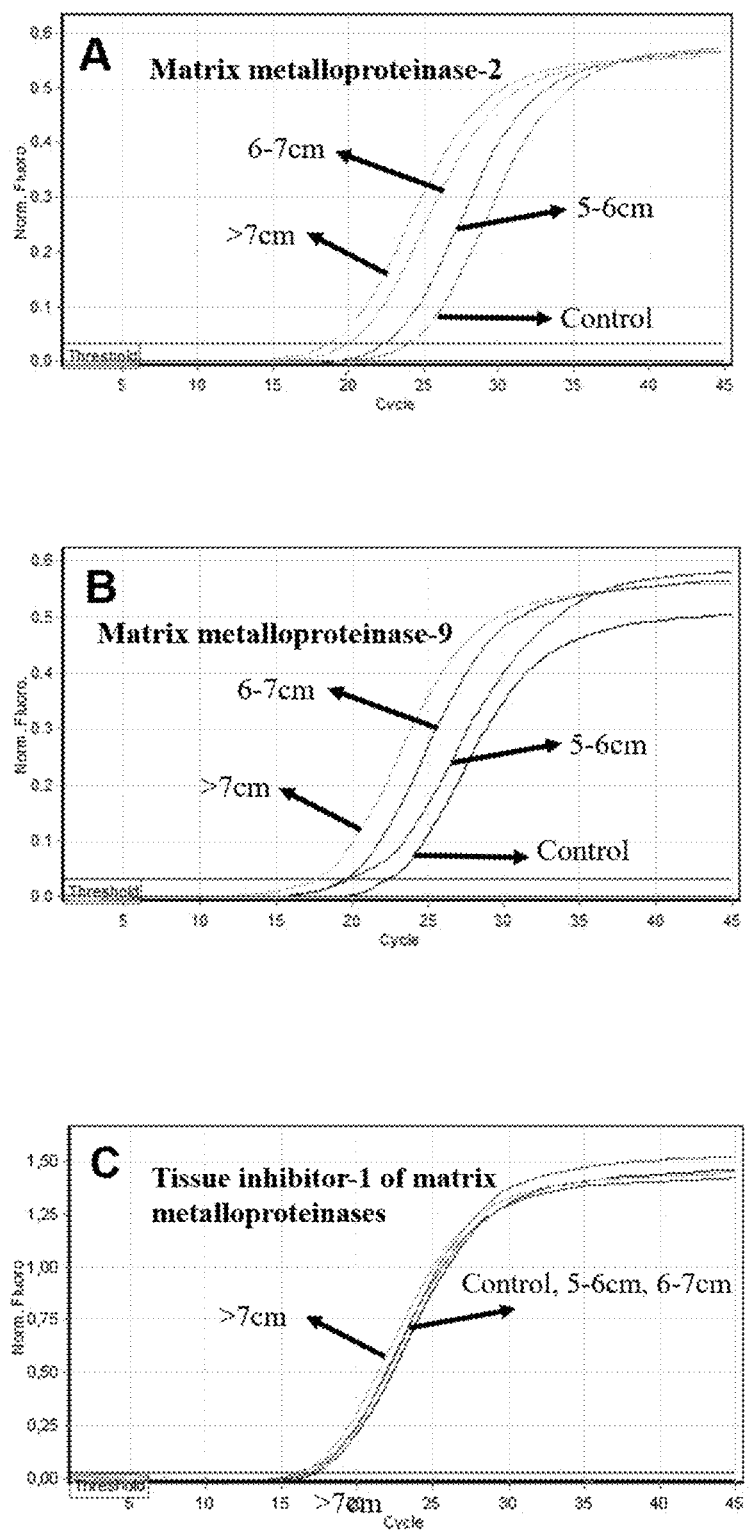
FIG. 6. Real-time quantitative RT-PCR reactions in aneurysm patients. Panels A to F show real-time quantitative amplification curves for Matrix metalloproteinase-2, Matrix metalloproteinase-9, Tissue inhibitor-1 of matrix metalloproteinases, Bone morphogenetic protein-1, Transforming growth factor beta-1 and Beta-actin.
Figure 6:
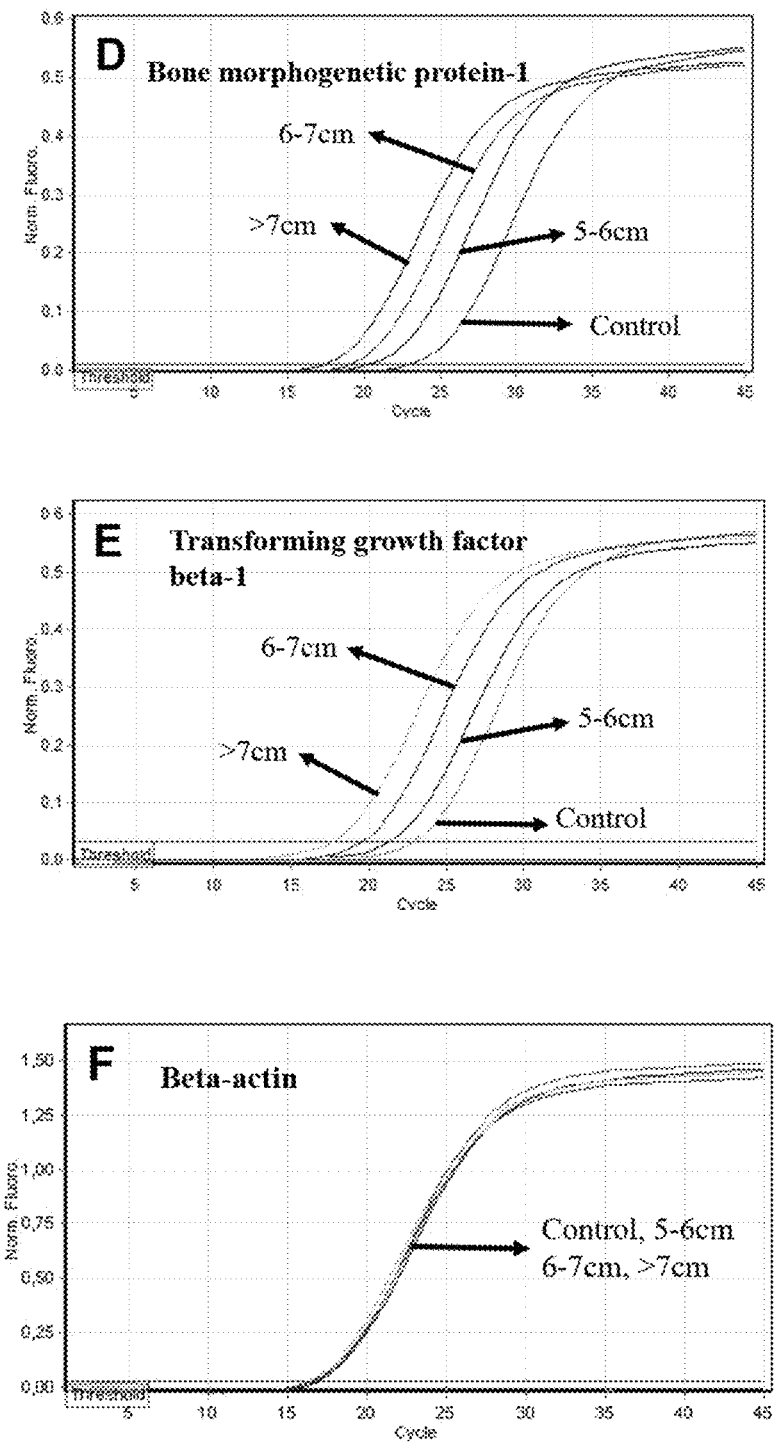

FIG. 6 shows representative real-time RT-PCR curves from matrix metalloproteinase-2, matrix metalloproteinase-9, tissue inhibitor-1 of matrix metalloproteinases, bone morphogenetic protein-1, transforming growth factor beta-1 and the reference gene of beta-actin in patients with thoracic aortic aneurysms. It is shown that there were higher levels of mRNA expression of matrix metalloproteinase-2, matrix metalloproteinase-9, tissue inhibitor-1 of matrix metalloproteinases, bone morphogenetic protein-1, transforming growth factor beta-1 in patients with thoracic aortic aneurysms as compared to controls. It is also shown that the levels of expression of these mRNAs which are controlling the remodeling of the ECM were even more overexpressed in larger diameter thoracic aortic aneurysms. There were no changes in the expression levels of beta-actin among controls and different sizes of thoracic aortic aneurysm patients. Table 12 shows the fold change expression pattern versus the reference group (patients with normal diameter thoracic aorta).

TABLE 12

Fold change expression pattern for various types of matrix metalloproteinases, bone morphogenetic protein-1, transforming growth factor beta-1 and the reference gene of beta-actin in patients with thoracic aortic aneurysms versus the reference group (patients with normal diameter thoracic aorta)

| | Fold change vs. Control | | | |
|---|---|---|---|---|
| | Controls (reference) | Aneurysm 5-6 cm | Aneurysm 6-7 cm | Aneurysm >7 cm |
| Matrix metalloproteinase-2 | 1.000 | 3.285 | 8.012 | 11.581 |
| Matrix metalloproteinase-9 | 1.000 | 2.851 | 7.532 | 12.259 |
| Tissue inhibitor-1 of matrix metalloproteinases | 1.000 | 1.130 | 1.310 | 1.508 |
| Bone morphogenetic protein-1 | 1.000 | 5.001 | 8.258 | 10.985 |
| Transforming growth factor beta-1 | 1.000 | 3.833 | 7.852 | 11.182 |
| Beta-actin | 1.000 | 0.988 | 1.023 | 1.051 |

All the products of the RT-PCR reactions were tested in agarose electrophoresis gel. All amplified products were represented by a single product at the expected molecular weight position. Further DNA sequencing analysis confirmed the expected sequences of the amplified PCR products.

In conclusion, it was found that the expression pattern of the genes collagen XI alpha-1, collagen V alpha-2, integrin receptor alpha-4, integrin receptor beta-1, matrix metalloproteinase-2, matrix metalloproteinase-9, transforming growth factor beta-1 and bone morphogenetic protein-1 provides reliable diagnostic information for aneurysm, in this case in particular, thoracic aortic aneurysm, in peripheral blood. There also exists a correlation between overexpression of these genes and the size of the aneurysm. This set of genes can adequately analyze the proposed novel molecular mechanism which controls the remodeling of the ECM. More specifically, by using these genes (all of which were significantly up-regulated in patients with thoracic aortic aneurysms and there was a significant up-regulation in larger diameter thoracic aortic aneurysms) it was possible to discriminate between patients with thoracic aortic aneurysms and controls with a sensitivity of 0.95 (95% confidence intervals: 0.89-1.00, P<0.001) and a specificity of 0.92 (95% confidence intervals: 0.78-1.00, P<0.001). Finally, by using these genes it was possible to discriminate between patients with larger aortic aneurysms (diameter more than 6 cm) and patients with smaller size aortic aneurysms (diameter between 5 and 6 cm) with a sensitivity of 0.95 (95% confidence intervals: 0.86-1.00, P<0.001) and a specificity of 0.86 (95% confidence intervals: 0.71-1.00, P<0.001).

The set genes not only showed high sensitivity and specificity in discriminating between control and patients with thoracic aortic aneurysms and between patients with relatively small size aortic aneurysms and patients with relatively large size thoracic aortic aneurysms, but in addition, it was possible to quantify between small size (aortic diameter 5-6 cm) and larger size thoracic aortic aneurysms (aortic diameter >6 cm) as compared with controls. More specifically, as it can be derived from the tables 10-12 and the FIGS. 4-6 it was possible to provide fold changes in the expression levels for the genes for quantification purposes between small size and larger size thoracic aortic aneurysms (table 13).

TABLE 13

Quantification of small size and larger size thoracic aortic aneurysms based on the fold change versus controls in the expression levels (mRNA) of the genes in peripheral blood.

| Gene | Aneurysms 5-6 cm | Aneurysms ≥6 cm |
|---|---|---|
| Collagen XI alpha-1 | >5 fold change | >15 fold change |
| Collagen V alpha-2 | >1.5 fold change | >5 fold change |
| Matrix metalloproteinase-2 | >3 fold change | >10 fold change |
| Matrix metalloproteinase-9 | >2.5 fold change | >12 fold change |
| Bone morphogenetic protein-1 | >5 fold change | >10 fold change |
| Integrin receptor alpha-4 | >1.5 fold change | >5 fold change |
| Integrin receptor beta-1 | >3 fold change | >8 fold change |
| Transforming growth factor beta-1 | >3 fold change | >10 fold change |

The panel of selected genes is the reflection of the remodeling/degradation of the ECM, which is essential in the monitoring and follow-up of patients especially prior to or after treatment intervention. One patient who has developed an aortic aneurysm remains at risk to develop another aortic aneurysm at another site of the aorta. A successful therapeutic intervention will result in expression levels of these genes that are close to controls. In the experimental measurements, it was found that the levels of minor fibril-forming collagens as well as the levels of the genes that are involved in the degradation of the ECM in patients without aortic aneurysm (confirmed by computer tomography scans) are expressed in significantly lower levels in the peripheral blood. Although the above results were obtained from patients suffering from thoracic aortic aneurysms, similar expression patterns could be detected in patients with abdominal or thoracoabdominal aortic aneurysms. Therefore, the differential expression of the above genes can be potentially used for the discrimination of patients with other types of aneurysms.

Finally, it is of great importance that in our clinical series, which have been confirmed by other large clinical datasets, approximately 19% of patients who were diagnosed with thoracic aortic aneurysm had a previous medical history of a treated malignancy, which included usually one of the following malignancies: non-small cell lung cancer, colon cancer and prostate cancer in male patients and non-small cell cancer, colon cancer and breast cancer in female patients. Conversely, in patients who were diagnosed with a malignancy also detected in computer tomography scans the existence of an aortic aneurysm (mainly thoracic aortic aneurysm) at a percentage of approximately 24%. This coexistence of malignancies with aortic aneurysms and vice versa indicates that these diseases indeed are sharing common molecular mechanisms for the remodeling of the ECM because in both cases their progression (aortic enlargement or metastatic disease) is based in alterations of the composition and physiologic/biologic properties of the ECM.

CITATION LIST

Non Patent Literature:

Livak and Schmittgen, "Analysis of relative gene expression data using real-time quantitative PCR and the 2(-Delta Delta C(T)) Method". *Methods,* 2001, vol. 25, issue 4, p. 402-8

Kroupis C. et al, "Development and applications of a real-time quantitative RT-PCR method (QRT-PCR) for BRCA1 mRNA". *Clin Biochem,* 2005, vol. 38, issue 1, p. 50-57

What is claimed:

1. A method of treating an aneurysm in a human subject, the method comprising:
   (i) determining that the human subject suffers from an aneurysm by determining that the level of mRNA of each one of COL11A1, COL5A2, COL5A1, TGFB1, ITGA4, ITGB1, MMP2, MMP9 and BMP1 genes in a peripheral blood sample from the subject are higher than a reference value; and
   (ii) subsequently treating the human subject with a therapeutic regime selected from the group consisting of open surgery to avoid the rupture of the blood vessel, endovascular repair with stent graft implantation, administration of a statin, administration of a beta-blocker, administration of an anti-hypertensive agent, and a combination thereof.

2. The method of claim 1, further comprising determining the level of an expression product of at least one gene selected from the group consisting of ITGA6, ITGA3, TIMP1, COL3A1, COL1A2 and COL1A1.

3. The method of claim 1, wherein the aneurysm has a high risk of rupturing when the mRNA of COL11A1, COL5A2, TGFB1, ITGA4, ITGB1, MMP2, MMP9 and BMP1 genes have the following levels:
   a) at least 15-fold overexpression with respect to a reference value for COL11A1;
   b) at least 5-fold overexpression with respect to a reference value for COL5A2;
   c) at least 10-fold overexpression with respect to a reference value for TGFB1,
   d) at least 10-fold overexpression with respect to a reference value for MMP2;
   e) at least 12-fold overexpression with respect to a reference value for MMP9;
   f) at least 10-fold overexpression with respect to a reference value for BMP1;
   g) at least 5-fold overexpression with respect to a reference value for ITGA4; or
   h) at least 8-fold overexpression with respect to a reference value for ITGB1.

* * * * *

SEQUENCE LISTING

```
<160> NUMBER OF SEQ ID NOS: 32

<210> SEQ ID NO 1
<211> LENGTH: 24
<212> TYPE: DNA
<213> ORGANISM: Artificial Sequence
<220> FEATURE:
<223> OTHER INFORMATION: COL1A1 forward primer

<400> SEQUENCE: 1
ctctgactgg aagagtggag agta                                          24

<210> SEQ ID NO 2
<211> LENGTH: 24
<212> TYPE: DNA
<213> ORGANISM: Artificial Sequence
<220> FEATURE:
<223> OTHER INFORMATION: COL1A1 reverse primer

<400> SEQUENCE: 2
ttggtggttt tgtattcaat cact                                          24

<210> SEQ ID NO 3
<211> LENGTH: 20
<212> TYPE: DNA
<213> ORGANISM: Artificial Sequence
<220> FEATURE:
<223> OTHER INFORMATION: COL1A2 forward primer

<400> SEQUENCE: 3
catcccagcc aagaactggt                                               20
```

```
<210> SEQ ID NO 4
<211> LENGTH: 20
<212> TYPE: DNA
<213> ORGANISM: Artificial Sequence
<220> FEATURE:
<223> OTHER INFORMATION: COL1A2 reverse primer

<400> SEQUENCE: 4
actgggccaa tgtccacaaa                                               20

<210> SEQ ID NO 5
<211> LENGTH: 24
<212> TYPE: DNA
<213> ORGANISM: Artificial Sequence
<220> FEATURE:
<223> OTHER INFORMATION: COL3A1 forward primer

<400> SEQUENCE: 5
agtgaccgac aaaattccag ttat                                          24

<210> SEQ ID NO 6
<211> LENGTH: 24
<212> TYPE: DNA
<213> ORGANISM: Artificial Sequence
<220> FEATURE:
<223> OTHER INFORMATION: COL3A1 reverse primer

<400> SEQUENCE: 6
cttttactgg tgagcacagt catt                                          24

<210> SEQ ID NO 7
<211> LENGTH: 20
<212> TYPE: DNA
<213> ORGANISM: Artificial Sequence
<220> FEATURE:
<223> OTHER INFORMATION: COL5A1 forward primer

<400> SEQUENCE: 7
ttcaagcgtg ggaaactgct                                               20

<210> SEQ ID NO 8
<211> LENGTH: 20
<212> TYPE: DNA
<213> ORGANISM: Artificial Sequence
<220> FEATURE:
<223> OTHER INFORMATION: COL5A1 reverse primer

<400> SEQUENCE: 8
gggagaagcc ttcactgtcc                                               20

<210> SEQ ID NO 9
<211> LENGTH: 24
<212> TYPE: DNA
<213> ORGANISM: Artificial Sequence
<220> FEATURE:
<223> OTHER INFORMATION: COL5A2 forward primer

<400> SEQUENCE: 9
tgagttgtgg agctgactct aatc                                          24

<210> SEQ ID NO 10
<211> LENGTH: 24
<212> TYPE: DNA
<213> ORGANISM: Artificial Sequence
<220> FEATURE:
```

<223> OTHER INFORMATION: COL5A2 reverse primer

<400> SEQUENCE: 10
taacagaagc atagcacctt tcag                                      24

<210> SEQ ID NO 11
<211> LENGTH: 25
<212> TYPE: DNA
<213> ORGANISM: Artificial Sequence
<220> FEATURE:
<223> OTHER INFORMATION: COL11A1 forward primer

<400> SEQUENCE: 11
gaaattgtac cttggtgcca ccaac                                     25

<210> SEQ ID NO 12
<211> LENGTH: 25
<212> TYPE: DNA
<213> ORGANISM: Artificial Sequence
<220> FEATURE:
<223> OTHER INFORMATION: COL11A1 reverse primer

<400> SEQUENCE: 12
ggatggatga gaatgagcac catat                                     25

<210> SEQ ID NO 13
<211> LENGTH: 20
<212> TYPE: DNA
<213> ORGANISM: Artificial Sequence
<220> FEATURE:
<223> OTHER INFORMATION: ITGA3 forward primer

<400> SEQUENCE: 13
acaaggatga ctgtgagcgg                                           20

<210> SEQ ID NO 14
<211> LENGTH: 20
<212> TYPE: DNA
<213> ORGANISM: Artificial Sequence
<220> FEATURE:
<223> OTHER INFORMATION: ITGA3 reverse primer

<400> SEQUENCE: 14
ctgcctacct gcatcgtgta                                           20

<210> SEQ ID NO 15
<211> LENGTH: 25
<212> TYPE: DNA
<213> ORGANISM: Artificial Sequence
<220> FEATURE:
<223> OTHER INFORMATION: ITGA4 forward primer

<400> SEQUENCE: 15
gtctttgtca ctaaaatgtt cccca                                     25

<210> SEQ ID NO 16
<211> LENGTH: 18
<212> TYPE: DNA
<213> ORGANISM: Artificial Sequence
<220> FEATURE:
<223> OTHER INFORMATION: ITGA4 reverse primer

<400> SEQUENCE: 16
cagcaagagc ggacctga                                             18

```
<210> SEQ ID NO 17
<211> LENGTH: 20
<212> TYPE: DNA
<213> ORGANISM: Artificial Sequence
<220> FEATURE:
<223> OTHER INFORMATION: ITGA6 forward primer

<400> SEQUENCE: 17
gttgggaggg tggttcaaca                                               20

<210> SEQ ID NO 18
<211> LENGTH: 21
<212> TYPE: DNA
<213> ORGANISM: Artificial Sequence
<220> FEATURE:
<223> OTHER INFORMATION: ITGA6 reverse primer

<400> SEQUENCE: 18
cgaatcccat tgctttggca c                                             21

<210> SEQ ID NO 19
<211> LENGTH: 19
<212> TYPE: DNA
<213> ORGANISM: Artificial Sequence
<220> FEATURE:
<223> OTHER INFORMATION: ITGB1 forward primer

<400> SEQUENCE: 19
atcagacgcg cagaggagg                                                19

<210> SEQ ID NO 20
<211> LENGTH: 20
<212> TYPE: DNA
<213> ORGANISM: Artificial Sequence
<220> FEATURE:
<223> OTHER INFORMATION: ITGB1 reverse primer

<400> SEQUENCE: 20
tgctgttcct ttgctacggt                                               20

<210> SEQ ID NO 21
<211> LENGTH: 21
<212> TYPE: DNA
<213> ORGANISM: Artificial Sequence
<220> FEATURE:
<223> OTHER INFORMATION: MMP2 forward primer

<400> SEQUENCE: 21
cgcatctggg gctttaaaca t                                             21

<210> SEQ ID NO 22
<211> LENGTH: 20
<212> TYPE: DNA
<213> ORGANISM: Artificial Sequence
<220> FEATURE:
<223> OTHER INFORMATION: MMP2 reverse primer

<400> SEQUENCE: 22
ctgtctgggg cagtccaaag                                               20

<210> SEQ ID NO 23
<211> LENGTH: 20
<212> TYPE: DNA
<213> ORGANISM: Artificial Sequence
<220> FEATURE:
<223> OTHER INFORMATION: MMP9 forward primer
```

```
<400> SEQUENCE: 23 ttcaggaga cgcccatttc                                          20

<210> SEQ ID NO 24
<211> LENGTH: 20
<212> TYPE: DNA
<213> ORGANISM: Artificial Sequence
<220> FEATURE:
<223> OTHER INFORMATION: MMP9 reverse primer

<400> SEQUENCE: 24
tcgctggtac aggtcgagta                                         20

<210> SEQ ID NO 25
<211> LENGTH: 20
<212> TYPE: DNA
<213> ORGANISM: Artificial Sequence
<220> FEATURE:
<223> OTHER INFORMATION: TIMP1 forward primer

<400> SEQUENCE: 25
cttctggcat cctgttgttg                                         20

<210> SEQ ID NO 26
<211> LENGTH: 20
<212> TYPE: DNA
<213> ORGANISM: Artificial Sequence
<220> FEATURE:
<223> OTHER INFORMATION: TIMP1 reverse primer

<400> SEQUENCE: 26
ggtataaggt ggtctggttg                                         20

<210> SEQ ID NO 27
<211> LENGTH: 21
<212> TYPE: DNA
<213> ORGANISM: Artificial Sequence
<220> FEATURE:
<223> OTHER INFORMATION: BMP1 forward primer

<400> SEQUENCE: 27
ccatgacaac aagcacgact g                                       21

<210> SEQ ID NO 28
<211> LENGTH: 20
<212> TYPE: DNA
<213> ORGANISM: Artificial Sequence
<220> FEATURE:
<223> OTHER INFORMATION: BMP1 reverse primer

<400> SEQUENCE: 28
gccacaatga cccactcaca                                         20

<210> SEQ ID NO 29
<211> LENGTH: 20
<212> TYPE: DNA
<213> ORGANISM: Artificial Sequence
<220> FEATURE:
<223> OTHER INFORMATION: TGFB1 forward primer

<400> SEQUENCE: 29
gagcctgagg ccgactacta                                         20

<210> SEQ ID NO 30
<211> LENGTH: 20
```

```
<212> TYPE: DNA
<213> ORGANISM: Artificial Sequence
<220> FEATURE:
<223> OTHER INFORMATION: TGFB1 reverse primer

<400> SEQUENCE: 30
gggttcaggt accgcttctc                                               20

<210> SEQ ID NO 31
<211> LENGTH: 24
<212> TYPE: DNA
<213> ORGANISM: Artificial Sequence
<220> FEATURE:
<223> OTHER INFORMATION: ACTB forward primer

<400> SEQUENCE: 31
agcattgctt tcgtgtaaat tatg                                          24

<210> SEQ ID NO 32
<211> LENGTH: 24
<212> TYPE: DNA
<213> ORGANISM: Artificial Sequence
<220> FEATURE:
<223> OTHER INFORMATION: ACTB reverse primer

<400> SEQUENCE: 32
gtgtgcactt ttattcaact ggtc                                          24
```